US007192914B1

(12) United States Patent
Marth et al.

(10) Patent No.: US 7,192,914 B1
(45) Date of Patent: Mar. 20, 2007

(54) PREVENTION OF ATHEROSCLEROSIS AND UNDESIRED BLOOD CLOTTING BY REDUCING VON WILLEBRAND FACTOR

(75) Inventors: Jamey D. Marth, San Diego, CA (US); Lesley G. Ellies, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 138 days.

(21) Appl. No.: 10/089,525

(22) PCT Filed: Sep. 27, 2000

(86) PCT No.: PCT/US00/26550

§ 371 (c)(1),
(2), (4) Date: Oct. 7, 2002

(87) PCT Pub. No.: WO01/22921

PCT Pub. Date: Apr. 5, 2001

Related U.S. Application Data

(60) Provisional application No. 60/157,220, filed on Sep. 30, 1999.

(51) Int. Cl.
*A01N 61/00* (2006.01)
*A01N 43/04* (2006.01)
*A01N 25/00* (2006.01)
*A61K 38/16* (2006.01)

(52) U.S. Cl. .................. 514/1; 514/8; 514/23; 514/49; 514/53; 514/54; 514/789

(58) Field of Classification Search .................. 514/44, 514/1, 2, 8, 23, 49, 53, 54, 789; 536/24.5; 435/6; 424/9.1
See application file for complete search history.

(56) References Cited

U.S. PATENT DOCUMENTS 6,280,989 B1 * 8/2001 Kapitonov et al. ......... 435/193
6,376,475 B1 * 4/2002 Marth et al. .................. 514/49

FOREIGN PATENT DOCUMENTS

WO    WO 98/54365    12/1998

OTHER PUBLICATIONS

Tsuji, S. Molecular cloning and functional analysis of sialyltransferases. Jan. 1996 J. Biochem. vol. 120, pp. 1-13 (see entire document, especially p. 5, section 3).*
Opalinska et al. 2002 Nucleic-acid therapeutics: Basic principles and recent applications. Nature Reviews-Drug Discovery vol. 1, pp. 503-514.*
Branch 1998 A good antisense molecule is hard to find, TIBS, vol. 23, pp. 45-50.*
Webster's II New Riverside University Dictionary 1994 The Riverside Publishing Company, pp. 933 and 944.*
Carver-Moore, K. et al., "Low levels of erythroid and myeloid progenitors in thrombopoietin- and c-mpl-deficient mice," *Blood*, 88(3):803-808 (Aug. 1, 1996).
Crocker, P. et al., "The potential role of sialoadhesin as a macrophage recognition molecule in health and disease," *Glycoconj. J.*, 14:601-609 (1997).
Gill, J. et al., "The effect of ABO blood group on the diagnosis of von Willebrand disease," *Blood*, 69(6):1691-1695 (Jun. 1987).
Ginsburg, D. and Bowie, E.J., "Molecular genetics of von Willebrand disease," *Blood*, 79(10):2507-2529 (May 15, 1992).
Gurney, A. et al., "Thrombocytopenia in c-mpl-deficient mice," *Science*, 265:14451447 (Sep. 2, 1994).
Hall, R. et al., "The frequencies of ABO blood groups and of secretors of ABH group substances in peripheral arteriosclerosis," *Atherosclerosis*, 14:241-246 (1971).
Kitagawa, H. and Paulson, J. et al., "Cloning of a novel α2,3-sialyltransferase that sialylates glycoprotein and glycolipid carbohydrate groups," *J. Biol. Chem.*, 269(2):1394-1401 (Jan. 14, 1994).
Lecine, P. et al., "Mice lacking transcription factor NF-E2 provide in vivo validation of the proplatelet model of thrombocytopiesis and show a platelet production defect that is intrinsic to megakaryocytes," *Blood*, 92(5):1608-1616 (Sep. 1, 1998).
Meade, T.W. et al., "Haemostatic function and cardiovascular death: Early results of a prospective study," *The Lancet*, 1:1050-1053 (May 17, 1980).
Mohlke, K. et al., "*Mvwf*, a dominant modifier of murine von Willebrand factor, results from altered lineage-specific expression of a glycosyltransferase," *Cell*, 96:111-120 (Jan. 8, 1999).
Nichols, W. and Ginsburg, D., "von Willebrand Disease," *Medicine*, 76(1):1-20 (1997).
Okajima, T. et al., "Molecular cloning of a novel α2,3-sialyltransferase (ST3Gal VI) that sialylates type II lactosamine structures on glycoproteins and glycolipids," *J. Biol. Chem.*, 274(17):11479-11486 (Apr. 23, 1999).
Orstavik, K. et al., "Possible effect of secretor locus on plasma concentration of factor VIII and von Willebrand factor," *Blood*, 73(4):990-993 (Mar. 1989).
Ruggeri, Z. and Zimmerman, T., "Variant von Willebrand's disease: Characterization of two subtypes by analysis of multimetric composition of factor VIII/von Willebrand factor in plasma and platelets," *J. Clin. Invest.*, 65:1318-1325 (Jun. 1980).

(Continued)

*Primary Examiner*—Jane Zara
(74) *Attorney, Agent, or Firm*—Townsend and Townsend and Crew LLP

(57) ABSTRACT

This invention provides methods and compositions for treating and preventing atherosclerosis other undesired blood clotting. The methods for treating and preventing atherosclerosis and related conditions involve administering to a mammal an agent that reduces activity of an ST3Gal IV sialyltransferase, which results in enhanced clearance of von Willebrand Factor (vWF) from the mammal.

12 Claims, 6 Drawing Sheets

OTHER PUBLICATIONS

Sasaki, K. et al., "Expression cloning of a novel Galβ(1-3/1-4)GlcNAc α2,3-sialyltransferase using lectin resistance selection," *J. Biol. Chem.*, 268(30):22782-22787 (Oct. 25, 1993).

Savage, B. et al., "Initiation of platelet adhesion by arrest onto fibrinogen or translocation on von Willebrand factor," *Cell*, 84:289-297 (Jan. 26, 1996).

Sodetz, J. et al., "Carbohydrate on human factor VIII/von Willebrand factor," *J. Biol. Chem.*, 253(20):7202-7206 (Oct. 25, 1978).

Sodetz, J. et al., "Relationship of sialic acid to function and *in vivo* survival of human factor VIII/von Willebrand factor protein," *J. Biol. Chem.*, 252(15):5538-5546 (Aug. 10, 1977).

Wagner, D. et al., "Initial glycosylation and acidic pH in the golgi apparatus are required for multimerization of von Willebrand factor," *J. Cell Biol.*, 102:1320-1324 (Apr. 1986).

Wilkie, A., "The molecular basis of genetic dominance," *J. Med. Genet.*, 31:89-98 (1994).

* cited by examiner

SEQUENCE LISTING

```
<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
```

-continued

```
<223> OTHER INFORMATION: Description of Artificial Sequence:PCR primer
      W5' adjacent to deleted region of ST3Gal-IV sialyltransferase wild
      type allele

<400> SEQUENCE: 1
gacgccatcc acctatgag                                                    19

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence:PCR primer
      W3' adjacent to deleted region of ST3Gal-IV sialyltransferase wild
      type allele

<400> SEQUENCE: 2
ggctgctccc attccact                                                     18

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:PCR primer
      M3' from loxP region of ST3Gal-IV sialyltransferase mutant allele

<400> SEQUENCE: 3
ggctctttgt gggaccatca g                                                 21
```

PREVENTION OF ATHEROSCLEROSIS AND UNDESIRED BLOOD CLOTTING BY REDUCING VON WILLEBRAND FACTOR

CROSS-REFERENCE TO RELATED APPLICATION

This application claims benefit of U.S. Provisional Application No. 60/157,220, filed Sep. 30, 1999.

STATEMENT REGARDING FEDERALLY SPONSORED RESEARCH

This invention was made with government support under Grant No. P01-HL 57345-01A1, awarded by the National Heart, Lung, and Blood Institute of the National Institutes of Health. The United States Government has certain rights in the invention.

BACKGROUND OF THE INVENTION

1. Field of the Invention

This invention pertains to the field of diagnosis and treatment of atherosclerosis and blood clotting disorders such as von Willebrand disease.

2. Background

Heart disease is the leading cause of death in the United States, and the third leading cause of death is stroke. Both conditions often result from atherosclerosis, which is often referred to as hardening of the arteries. Atherosclerosis involves a buildup of plaque, fatty deposits made up of LDL-cholesterol, lipids and cellular debris, on the inner walls of arteries. The plaque buildups cause a progressive obstruction of the arteries, which can lead to a deficiency of oxygen in the tissues that are supplied by the affected arteries. Obstruction of the coronary arteries by plaque can cause ischemia due to a deficiency in the amount of oxygen that reaches the heart muscle; this can lead to a heart attack. Obstruction of arteries that lead to the brain can cause stroke. Peripheral arteries are also subject to atherosclerosis; this can result in formation of a blood clot that can block the blood supply to an organ. Aneurysms can also result from atherosclerosis, due to the weakening of the arteries at the point of plaque buildups.

Several risk factors for atherosclerosis are such that one can reduce the risk of atherosclerosis by lifestyle changes, such as a healthy diet and exercise, cessation of smoking, and control of blood pressure. Drugs are available for reducing cholesterol levels, another significant risk factor. Other risk factors not subject to modification by an individual. These risk factors include increasing age, diabetes, and family history of atherosclerosis are significant risk factors. Factor VIII (FVIII) has been found to be a risk factor for coronary artery disease and blood group O individuals who have low serum cholesterol. Individuals with low vWF/FVIII have a low frequency of peripheral arterial disease compared with the general population (Hall et al. (1971) *Atherosclerosis* 14: 241–246; Meade et al. (1980) *Lancet* 1: 1050–1054. However, any potential treatment or prophylactic method that attempted to reduce vWF and/or FVIII would be expected to cause a bleeding disorder such as hemophilia or Von Willebrand disease (VWD).

VWD, which is characterized by a marked deficiency in von Willebrand factor (vWF) activity, is the most common inherited bleeding disorder in humans, with a prevalence of up to 1.3% of the population (reviewed in Nichols and Ginsburg (1997) *Medicine* 76: 1–20). In the United States, up to two million people suffer from VWD. vWF is a multimeric plasma glycoprotein that stabilizes coagulation factor VIII (FVIII). vWF plays an essential role in hemostasis by mediating platelet adhesion and aggregation to subendothelium at sites of vascular injury (Savage et al. (1996) *Cell* 84, 289–97). At least six major subtypes of VWD are known. Multimer analysis shows qualitative and quantitative defects in vWF from the VWD variants (Nichols and Ginsburg, supra.).

VWD is inherited in an autosomal dominant manner, as are the majority of bleeding disorders, although the mechanisms underlying this observation are not well understood. Systemic mutagenesis in diploid organisms indicates that most mutations are recessive to wild type with a ratio of approximately 20–10:1 (reviewed in Wilkie (1994) *J. Med. Genet.* 31: 89–98). Defects in the von Willebrand factor (vWF) gene itself have been identified in a subset of VWD individuals. However, the genetic basis for the majority of clinical cases is unknown. The variability observed may be the result of contributions from other genetic loci (Ginsburg and Bowie (1992) *Blood* 79: 2507–19; Nichols and Ginsburg, supra.).

Some studies have examined the role of glycosylation in vWF structure and function. Normal polymerization of vWF involves initial N-linked glycosylation and acidic pH in the Golgi apparatus of endothelial cells (Wagner et al. (1986) *J. Cell Biol.* 102: 1320–4). It is known that approximately 30% of the variance in normal plasma vWF levels is related to the ABH blood group oligosaccharide determinants (Orstavik et al. (1989) *Blood* 73: 990–3). There is an increased number of group O individuals in patients with type I VWD, suggesting that upregulation of α2 fucosyltransferases results in a loss of vWF from the circulation (Gill et al. (1987) *Blood* 69: 1691–5). A role for glycosyltransferases has also been identified in the RIIIs/J mouse strain which has low plasma vWF. An N-acetylgalactosaminyltransferase, Galgt2 has switched gene expression from epithelial cells to endothelial cells resulting in misglycosylation of vWF and enhanced clearance in this strain (Mohlke et al. (1999) *Cell* 96: 111–20). This gain-of-function mutation results in Galgt2 expression in both heterozygous and homozygous null mice and thus has an autosomal dominant inheritance pattern.

Desialylation of vWF does not affect procoagulant activity, but does result in more rapid clearance in vivo, possibly due to the exposure of terminal galactose residues which can be recognized by hepatic asialoglycoprotein receptors (Sodetz et al. (1977) *J. Biol. Chem.* 252: 5538–46). The galactose residues are present in a terminal Galβ1,4GlcNAc and comprise over 60% of the total galactose on native vWF/FVIII. Sialic acid can be incorporated into desialylated vWF/FVIII by purified α2,6 sialyltransferase which has specificity for the Galβ1,4GlcNAc structure (Sodetz et al. (1978) *J. Biol. Chem.* 253: 7202–6). These studies have not, however, identified the specific sialyltransferase enzymes that are responsible for sialylating vWF/FVIII in vivo. Nor have these studies revealed how vWF levels might be involved in atherosclerosis.

The lack of knowledge that exists as to how certain risk factors are involved atherosclerosis has hampered development of diagnostic and treatment methods for atherosclerosis. The present invention fulfills this need, and provides novel methods for treating and preventing atherosclerosis.

SUMMARY OF THE INVENTION

The present invention provides novel treatment and diagnostic methods for atherosclerosis and related conditions, and for preventing or treating blood clotting that can arise as a side effect of certain drugs.

In some embodiments, the invention provides methods for modulating levels of vWF and/or FVIII in an animal. The methods involve administering to the animal an agent that causes an increase or a decrease in ST3Gal IV sialyltransferase activity in the animal. For reducing blood clotting, the method involves decreasing levels of vWF or FVIII by decreasing ST3Gal IV activity. The decrease in ST3Gal IV activity can be achieved by administering an agent that decreases expression of a gene that encodes ST3Gal IV, and/or by administering an agent that inhibits enzymatic activity of an ST3Gal IV polypeptide.

Also provided by the invention are methods for monitoring the efficacy of a method for inhibiting ST3Gal IV in a mammal, the method comprising testing cells obtained from the mammal for the presence or absence of a cell-surface oligosaccharide having a terminal $\alpha 2,3$-linked sialic acid, wherein the absence of the terminal $\alpha 2,3$-linked sialic acid is indicative of inhibition of ST3Gal-IV activity.

In another embodiment, the invention provides eukaryotic cells in which a non-naturally occurring mutation is present in an ST3Gal IV allele. At least one, and sometimes two or more alleles have a mutation. In presently preferred embodiments, the mutation either disrupts the expression of ST3Gal IV or results in expression of an ST3Gal IV polypeptide that has reduced activity compared to an ST3Gal IV polypeptide encoded by a gene that lacks the mutation.

The invention also provides transgenic and chimeric animals that have non-naturally occurring mutation in an ST3Gal IV allele in at least some of the cells of the animal.

BRIEF DESCRIPTION OF THE DRAWINGS

FIG. 1A: The wild type ST3Gal-IV genomic locus was used in conjunction with the pflox vector to construct a targeting vector in which exons containing the large sialyl motif were flanked by loxP sites (ST3Gal-IV$^{F[tkneo]}$). Restriction enzyme sites indicated are Bam HI (B,) Avr II (A), Eco RI (E), Hind III (H), Kpn I (K), Not I (N), Sal I (Sa), Spe I (Sp) and Xba I (X). FIG. 1B: Transient Cre expression in ST3Gal-IV-targeted ES cells resulted in subclones isolated that carry a ST3Gal-IV$^{-/-}$ (systemic-null) or ST3Gal-IV$^F$ (conditional-null) mutation. FIG. 1C: Southern blot analysis of a Avr II/Spe I digest of ES cell DNA probed with a loxP probe confirmed the expected structures. Wild type R1 ES cell DNA did not hybridize to the loxP probe. Three loxP sites are present in a targeted parental clone (21-6), one loxP site is present in each of two ST3Gal-IV$^{-/-}$ subclones (21-F1 and 21-D1) and two loxP sites are present in the ST3Gal-IV$^F$ subclones (21-A3 and 21-E1).

FIG. 2A: Total RNA (lower panel) from various tissues obtained from a normal mouse was hybridized to a probe specific for ST3Gal-IV (upper panel). FIG. 2B: RNA from the small intestine and colon of wild-type and ST3Gal-IV$^{-/-}$ mice were hybridized to a labeled full-length mouse ST3Gal-IV cDNA. FIG. 2C: Myeloid cells of the bone marrow were double-stained with monoclonal antibodies that recognize myeloid cells (CD11b) and the lectin chimeras, siglec 1, E-selectin and P-selectin, as well as the PNA and ECA lectins and an antibody that recognizes the CD43 130 kD (1B11) and subjected to flow cytometric analysis. Myeloid cells were detected by an anti-CD11b antibody.

FIG. 3B shows a plot of the mean platelet volumes from the same samples. FIG. 3C shows megakaryocytes from wild type, heterozygous or homozygous null mice that were stained with hematoxylin and eosin (1000×), CD41 (100×), or vWF (200×). Sections from the small intestine were double stained with the lectin DBA and vWF (200×).

DETAILED DESCRIPTION

Definitions

Figure 1:
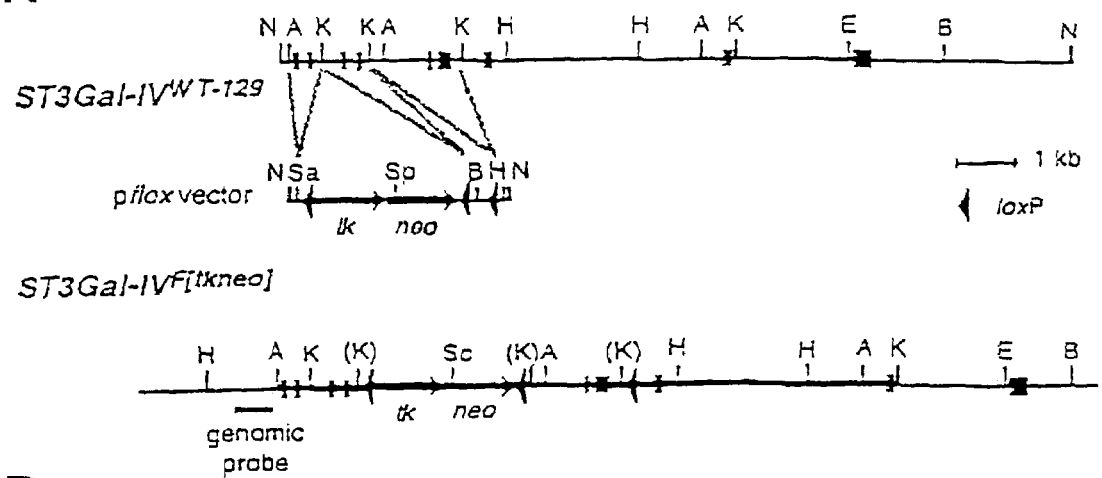
FIGS. 1A–C show a strategy employed to disrupt the ST3Gal-IV gene and introduce the disrupted gene in embryonic stem cells, from which knockout mice were obtained.
FIG. 1D shows hybridization of the genomic probe shown in FIG. 1A to Hind III-digested DNA obtained from the tail of progeny from a heterozygous mating of a ST3Gal-IV$^{-/-}$ chimera. Both the 6.8 kb wild type allele and the 5.3 kb mutant allele were visible in heterozygous (+/−) progeny, while only the 6.8 kb wild-type allele was found in the homozygous normal (+/+) animal, and only the 5.3 kb mutant allele was observed in the homozygous ST3Gal-IV deficient (−/−) mouse.
Figure 1:
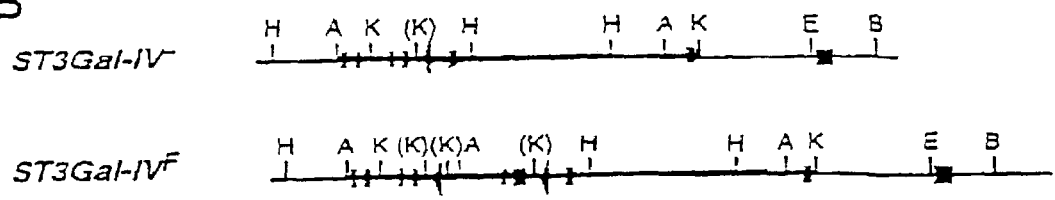
Figure 1:
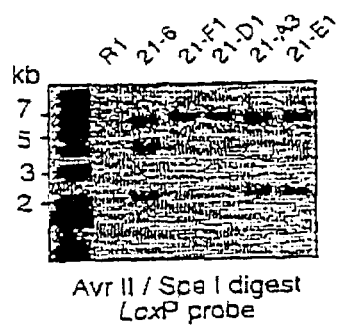
Figure 1:
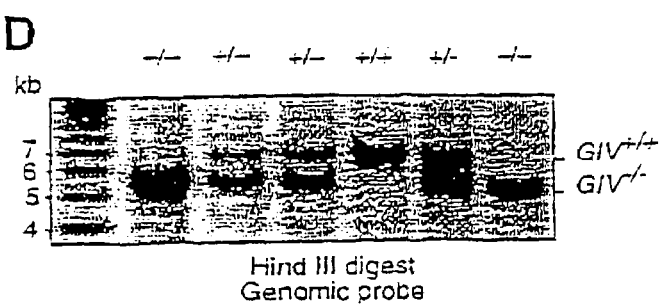

The following abbreviations are used herein:

Ara=arabinosyl;
Fru=fructosyl;
Fuc=fucosyl;
Gal=galactosyl;
GalNAc=N-acetylgalactosaminyl;
Glc=glucosyl;
GlcNAc=N-acetylglucosaminyl;
Man=mannosyl; and
NeuAc=sialyl(N-acetylneuraminyl).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

All oligosaccharides described herein are described with the name or abbreviation for the non-reducing saccharide (e.g., Gal), followed by the configuration of the glycosidic bond ($\alpha$ or $\beta$), the ring bond, the ring position of the reducing saccharide involved in the bond, and then the name or abbreviation of the reducing saccharide (e.g., GlcNAc). The linkage between two sugars may be expressed, for example, as 2, 3, 2→3, or (2,3). Each saccharide is a pyranose.

The term "sialic acid" refers to any member of a family of nine-carbon carboxylated sugars. The most common member of the sialic acid family is N-acetyl-neuraminic acid (2-keto-5-acetamindo-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550–11557; Kanamori et al. (1990) *J. Biol. Chem.* 265: 21811–21819. Also included are 9-substituted sialic acids such as a 9-O—C1–C6 acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki (1992) *Glycobiology* 2: 25–40; *Sialic Acids: Chemistry, Metabolism and Function*, R. Schauer, Ed. (Springer-Verlag, New York (1992). The synthesis and use of sialic acid compounds in a sialylation procedure is disclosed in international application WO 92/16640, published Oct. 1, 1992.

Much of the nomenclature and general laboratory procedures required in this application can be found in Sambrook, et al. (1989) *Molecular Cloning: A Laboratory Manual* (2nd Ed.), Vol. 1–3, Cold Spring Harbor Laboratory, Cold Spring Harbor, N.Y. The manual is hereinafter referred to as "Sambrook et al."

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof.

An "inhibitory nucleic acid" is any nucleic acid or modified nucleic acid used or designed for use in inhibitory nucleic acid therapy. "Inhibitory nucleic acid therapy" refers to the use of inhibitory nucleic acids to inhibit gene expression, for example, inhibition of DNA transcription, inhibition of RNA processing, transport or translation, or inhibition of protein synthesis. Inhibitory nucleic acid therapy includes the variety of approaches for treatment of disease using nucleic acids or modified nucleic acids as described herein. Various inhibitory nucleic acid therapies are discussed in detail below.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "heterologous sequence" or a "heterologous nucleic acid", as used herein, is one that originates from a source foreign to the particular host cell, or, if from the same source, is modified from its original form.

A "subsequence" refers to a sequence of nucleic acids or amino acids that comprise a part of a longer sequence of nucleic acids or amino acids (e.g., polypeptide) respectively.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

The term "isolated" is meant to refer to material which is substantially or essentially free from components which normally accompany the enzyme as found in its native state. Thus, the enzymes of the invention do not include materials normally associated with their in situ environment. Typically, isolated proteins of the invention are at least about 80% pure, usually at least about 90%, and preferably at least about 95% pure as measured by band intensity on a silver stained gel or other method for determining purity. Protein purity or homogeneity can be indicated by a number of means well known in the art, such as polyacrylamide gel electrophoresis of a protein sample, followed by visualization upon staining. For certain purposes high resolution will be needed and HPLC or a similar means for purification utilized.

The phrase "substantially identical," in the context of two nucleic acids or polypeptides, refers to two or more sequences or subsequences that have at least 70%, preferably 80%, most preferably 90–95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman (1981) *Adv. Appl. Math.* 2: 482, by the homology alignment algorithm of Needleman & Wunsch (1970) *J. Mol. Biol.* 48: 443, by the search for similarity method of Pearson & Lipman (1988) *Proc. Nat'l. Acad. Sci. USA* 85: 2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

Another example of algorithm that is suitable for determining percent sequence identity and sequence similarity is the BLAST algorithm, which is described in Altschul et al. (1990) *J. Mol. Biol.* 215: 403–410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89: 10915).

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every polynucleotide sequence described herein which encodes a polypeptide also describes every possible silent variation, except where otherwise noted. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence.

Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. See, e.g., Creighton (1984) *Proteins*, W.H. Freeman and Company. In addition, individual substitutions, deletions or additions which alter, add or delete a single amino acid or a small percentage of amino acids in an encoded sequence are also "conservatively modified variations".

The term "transgenic" refers to a cell that includes a specific genetic modification that was introduced into the cell, or an ancestor of the cell. Such modifications can include one or more point mutations, deletions, insertions, or combinations thereof. When referring to an animal, the term "transgenic" means that the animal includes cells that are transgenic, and descendants of such animals. An animal that is composed of both transgenic and non-transgenic cells is referred to herein as a "chimeric" animal.

DESCRIPTION OF THE PREFERRED EMBODIMENTS

The present invention provides compositions and methods for modulating levels of active von Willebrand factor (vWF) multimers. Reduced vWF levels are correlated with a reduced risk of developing atherosclerosis. The invention is based on the discovery that ablation of one or more alleles of the ST3Gal IV sialyltransferase results in a decrease in vWF. Surprisingly, the methods of the invention allow one to achieve a sufficient reduction in vWF multimers to treat or prevent atherosclerosis without causing a reduction in vWF levels that can cause von Willebrand's disease (VWD). Even a complete elimination of ST3Gal IV sialyltransferase activity results in only a 50% reduction in vWF concentration, while VWD occurs when vWF levels fall to about ten percent of normal or less. Another advantage of the methods of the invention is that platelet formation is not hindered except when ST3Gal IV activity is nearly eliminated.

Accordingly, the compositions and methods of the invention are useful for treating and/or preventing atherosclerosis by causing a decrease in vWF multimers without danger of causing VWD or a similar type of bleeding disorder. The compositions and methods are also useful for ameliorating blood clotting that occurs as a side effect of certain drugs or in response to other stimuli. Also provided are methods for diagnosing conditions associated with glycosylation of vWF. Transgenic non-human animals that have a disruption in one or more copies of an ST3Gal IV sialyltransferase gene are also provided.

Prophylactic and Therapeutic Methods for Atherosclerosis and Other Undesirable Clotting In some embodiments, the invention provides methods for reducing levels of vWF by partially or completely reducing the biosynthesis on vWF of N-linked and/or O-linked oligosaccharides that terminate in an α2,3-linked sialic acid. vWF that lacks the sialic acid is more rapidly cleared from the circulation than is normally sialylated vWF. Reduced vWF/FVIII is associated with a decreased frequency of atherosclerotic conditions, including coronary artery disease and peripheral vascular disease (Hall et al. (1971) *Atherosclerosis* 14: 241–6; Meade et al. (1980) *Lancet* 1: 1050–4).

The methods involve administering a compound that reduces the level of biosynthesis of α2,3-sialic acid-terminated oligosaccharides on vWF.

A. Reducing Biosynthesis of Oligosaccharides Having a Terminal α2,3-Linked Sialic Acids The invention provides several methods by which reductions in biosynthesis of oligosaccharides that terminate in an α2,3-linked sialic acid can be accomplished. The expression of the ST3Gal IV sialyltransferase can be inhibited, for example, or the enzymatic activity of the protein can be inhibited. Alternatively, the oligosaccharide that serves as an acceptor for the ST3Gal IV-catalyzed reaction can be modified, e.g., by addition or removal of a saccharide residue from the acceptor to render the oligosaccharide no longer an acceptable acceptor for ST3Gal IV.

Sialyltransferase Inhibitors

In some embodiments, reductions in vWF/FVIII are obtained by inhibiting the enzymatic activity of ST3 Gal IV. Enzyme inhibition generally involves the interaction of a substance with an enzyme so as to decrease the rate of the reaction catalyzed by that enzyme.

Several inhibitors of sialyltransferases are known in the art. For example, analogs of sialyltransferase substrates are suitable for use as inhibitors. Analogs of both the donor (e.g., analogs of CMP-sialic acid) and the acceptor have been reported which serve as sialyltransferase inhibitors (Schaub et al. (1998) *Glycoconjugate J.* 15: 345–354; Schaub and Schmidt (1996) *Abstract C* 10, Second European Conference on Carbohydrate Mimics, La Garda (Italy); Amann et al. (1998) *Chem. Eur. J.* 4: 1106–1115; Müller et al. (1998) *Tetrahedron Lett.* 39: 509–512; Korytnyk et al. (1980) *Eur. J. Med. Chem.* 15: 77–84; Kijima-Suda et al. (1986) *Cancer Res.* 46: 858–862; Khan et al. (1992) In *Glycoconjugates, Composition, Stricture, Function* (Eds.: H. J. Allen, E. C. Kisailus). M. Dekker, New York, pp. 361–378 and references therein; Hashimoto et al. (1993) *Carbohydr. Res.* 247: 179–193; Imamoto and Hashimoto (1996) *Tetrahedron Lett.* 37: 1451–1454; Kleineidam et al. (1997) *Glycoconjugate J.* 14: 57–66). Transition state analogs are also useful as sialyltransferase inhibitors (Schaub et al., supra., Schaub and Schmidt, supra.; Amann et al., supra., and WO 008040). Other sialyltransferase inhibitors are described in Cambron and Leskawa (1993) *Biochem. Biophys. Res. Commun.* 193:585–90.

ST3Gal IV activity can also be regulated by modulation of the phosphorylation state of the enzyme. Phosphorylation of a serine residue in ST3Gal IV by, for example, protein kinase A or C results in a decrease in sialyltransferase activity (Gu et al. (1995) *J. Neurochem.* 64:2295–302). Activity can be restored by treatment with a phosphatase. Protein kinase activators and phosphatase inhibitors can therefore be administered to reduce ST3 Gal IV activity. One example of a suitable protein kinase inhibitor is a subtype of the 14-3-3 protein family that has been shown to be associated with ST3Gal IV (Gao et al. (1996) *Biochem. Biophys. Res. Commun.* 224:103–7). Other examples of suitable protein kinase activators and phosphatase inhibitors are described in Bieberich et al. (1998) *J. Neurochem.* 71:972–9.

Additional inhibitors of the ST3Gal IV sialyltransferase can be readily identified by screening methods known to those of skill in the art. Sialyltransferase activity and its inhibition is typically assayed according to standard methods for determining enzyme activity. For a general discussion of enzyme assays, see, Rossomando, "Measurement of Enzyme Activity" in *Guide to Protein Purification*, Vol. 182, Methods in Enzymology (Deutscher ed., 1990), and Fersht, *Enzyme Structure and Mechanism* (2d ed. 1985). Enzyme inhibition of kinetically complex systems involving more than one substrate, as is the case for glycosyltransferases, are described in Segel, *Enzyme Kinetics*, (Wiley, N.Y. 1975), which is incorporated herein by reference.

An assay for ST3Gal IV activity typically contains a buffered solution adjusted to physiological pH, a source of divalent cations, a donor substrate (usually labeled CMP-sialic acid), an acceptor substrate (e.g., Galβ1,4GlcNAc or Galβ1,3GalNAc), the sialyltransferase, and the compound whose inhibitory activity is to be tested. After a predetermined time, typically at 23° C. or 37° C., the reaction is stopped and the sialylated product is isolated and measured according to standard methods (e.g., in a scintillation counter). Sialyltransferase assays which use a UV-labeled acceptor and lead to a UV-labeled product that can be readily separated by reverse phase HPLC and quantitated by UV spectroscopy are described in Schaub et al. (1998) *Glycoconjugate J.* 15: 345–354. See also, Kajihara et al. (1994) *Carbohydr. Res.* 264, C1–C5; (1995) *J. Org Chem.* 60: 5732–5735. Inhibition of sialyltransferase activity in an assay as defined herein refers to a decrease in enzyme specific activity in the presence of an inhibitory agent of at least about 50%, more preferably at least about 70%, and still more preferably at least about 90%, compared to the activity in the absence of the agent.

Screening can be employed to identify ST3Gal IV inhibitors that are present in a mixture of synthetically produced compounds or alternatively in a naturally occurring mixture, such as a cell culture broth. Suitable cells include any cultured cells such as mammalian, insect, microbial or plant cells. Microbial cell cultures are composed of any microscopic organism such as bacteria, protozoa, yeast, fungi and the like. In the typical screening assay, a sample, such as a fungal broth, is added to a standard sialyltransferase assay. If inhibition of activity as compared to control assays is found, the mixture is usually fractionated to identify components of the sample that provide the inhibiting activity. The sample is fractionated using standard methods such as ion exchange chromatography, affinity chromatography, electrophoresis, ultrafiltration, HPLC and the like. See, e.g., *Protein Purification, Principles and Practice*, (Springer-Verlag, 1982). Each isolated fraction is then tested for inhibitory activity. If desired, the fractions are then further subfractionated and tested. This subfractionation and testing procedure can be repeated as many times as desired.

By combining various standard purification methods, a substantially pure compound suitable for in vivo therapeutic testing can be obtained. A substantially pure blocking agent as defined herein is an inhibitory compound which migrates largely as a single band under standard electrophoretic conditions or largely as a single peak when monitored on a chromatographic column. More specifically, compositions of substantially pure blocking agents will comprise less than ten percent miscellaneous compounds.

Inhibitors can be classified according a number of criteria. For example, they may be reversible or irreversible. An irreversible inhibitor dissociates very slowly, if at all, from its target enzyme because it becomes very tightly bound to the enzyme, either covalently or noncovalently. Reversible inhibition, in contrast, involves an enzyme-inhibitor complex which may dissociate. Inhibitors can also be classified according to whether they are competitive, noncompetitive or uncompetitive inhibitors. In competitive inhibition for kinetically simple systems involving a single substrate, the enzyme can bind either the substrate or the inhibitor, but not both. Typically, competitive inhibitors resemble the substrate or the product(s) and bind the active site of the enzyme, thus blocking the substrate from binding the active site. A competitive inhibitor diminishes the rate of catalysis by effectively reducing the affinity of the substrate for the enzyme. Typically, an enzyme may be competitively inhibited by its own product because of equilibrium considerations. Since the enzyme is a catalyst, it is in principle capable of accelerating a reaction in the forward or reverse direction. Noncompetitive inhibitors allow the enzyme to bind the substrate at the same time it binds the inhibitor. A noncompetitive inhibitor acts by decreasing the turnover number of an enzyme rather than diminishing the proportion of free enzyme. Another possible category of inhibition is mixed or uncompetitive inhibition, in which the inhibitor affects the binding site and also alters the turnover number of the enzyme.

Inhibition of ST3 Gal IV Gene Expression

Inhibition of ST3Gal IV gene expression can also be achieved through the use of inhibitory nucleic acids. Inhibitory nucleic acids can be single-stranded nucleic acids that are complementary to, and thus can specifically hybridize to, a target sequence such as a nucleic acid that encodes ST3Gal IV. By binding to the appropriate target sequence, an RNA—RNA, a DNA—DNA, or RNA-DNA duplex or triplex is formed. These nucleic acids are often termed "antisense" because they are usually complementary to the sense or coding strand of the gene, although recently approaches for use of "sense" nucleic acids have also been developed. The term "inhibitory nucleic acids" as used herein, refers to both "sense" and "antisense" nucleic acids.

In one embodiment, the inhibitory nucleic acid can specifically bind to a target nucleic acid that encodes an ST3Gal IV sialyltransferase. The nucleotide sequence of a human ST3Gal IV cDNA is reported in Kitagawa and Paulson (1994) *J. Biol. Chem.* 269: 1394–401. This nucleotide can be used as a probe for the identification of ST3Gal IV-encoding nucleic acids from other species. From the human or other ST3Gal IV-encoding nucleotide sequences, one can derive suitable inhibitory nucleic acids. Administration of such inhibitory nucleic acids to a mammal can reduce circulating levels of vWF by reducing or eliminating the biosynthesis of Siaα2,3Gal-containing oligosaccharides.

By binding to the target nucleic acid, the inhibitory nucleic acid can inhibit the function of the target nucleic acid. This could, for example, be a result of blocking DNA transcription, processing or poly(A) addition to mRNA, DNA replication, translation, or promoting inhibitory mechanisms of the cells, such as promoting RNA degradation. Inhibitory nucleic acid methods therefore encompass a number of different approaches to altering expression of specific genes that operate by different mechanisms. These different types of inhibitory nucleic acid technology are described in Helene and Toulme (1990) *Biochim. Biophys. Acta.* 1049: 99–125.

Inhibitory nucleic acid therapy approaches can be classified into those that target DNA sequences, those that target RNA sequences (including pre-mRNA and mRNA), those that target proteins (sense strand approaches), and those that cause cleavage or chemical modification of the target nucleic acids.

Approaches targeting DNA fall into several categories. Nucleic acids can be designed to bind to the major groove of the duplex DNA to form a triple helical or "triplex" structure. Alternatively, inhibitory nucleic acids are designed to bind to regions of single stranded DNA resulting from the opening of the duplex DNA during replication or transcription. See Helene and Toulme, supra.

More commonly, inhibitory nucleic acids are designed to bind to mRNA or mRNA precursors. Inhibitory nucleic acids are used to prevent maturation of pre-mRNA. Inhibitory nucleic acids may be designed to interfere with RNA processing, splicing or translation. The inhibitory nucleic acids are often targeted to mRNA. In this approach, the inhibitory nucleic acids are designed to specifically block translation of the encoded protein. Using this approach, the inhibitory nucleic acid can be used to selectively suppress certain cellular functions by inhibition of translation of mRNA encoding critical proteins. For example, an inhibitory antisense nucleic acid complementary to regions of a target mRNA inhibits protein expression. See, e.g., Wickstrom E. L. et al. (1988) *Proc. Nat'l. Acad. Sci. USA* 85:1028–1032 and Harel-Bellan et al. (1988) *Exp. Med.,* 168:2309–2318. As described in Helene and Toulme, inhibitory nucleic acids targeting mRNA have been shown to work by several different mechanisms in order to inhibit translation of the encoded protein(s).

The inhibitory nucleic acids introduced into the cell can also encompass the "sense" strand of the gene or mRNA to trap or compete for the enzymes or binding proteins involved in mRNA translation. See Helene and Toulme.

Lastly, the inhibitory nucleic acids can be used to induce chemical inactivation or cleavage of the target genes or mRNA. Chemical inactivation can occur by the induction of crosslinks between the inhibitory nucleic acid and the target nucleic acid within the cell. Alternatively, irreversible photochemical reactions can be induced in the target nucleic acid by means of a photoactive group attached to the inhibitory nucleic acid. Other chemical modifications of the target nucleic acids induced by appropriately derivatized inhibitory nucleic acids may also be used.

Cleavage, and therefore inactivation, of the target nucleic acids may be effected by attaching a substituent to the inhibitory nucleic acid which can be activated to induce cleavage reactions. The substituent can be one that effects either chemical, photochemical or enzymatic cleavage. Alternatively cleavage can be induced by the use of ribozymes or catalytic RNA. In this approach, the inhibitory nucleic acids would comprise either naturally occurring RNA (ribozymes) or synthetic nucleic acids with catalytic activity.

Once ST3Gal IV inhibitors are identified, they can be tested for ability to reduce vWF/FVIII upon administration to laboratory animals. Animals can be treated with pharmacological doses of the inhibitor to block addition of α2,3-linked sialic acid to cell surface carbohydrates of vWF. The effect of the inhibitor on levels of vWF and/or FVIII is then determined.

B. Administration of ST3Gal IV Inhibitors

The invention provides methods and compositions for treating and preventing atherosclerosis and related conditions, disorders that involve inflammatory changes in blood vessel endothelium, as well as for preventing blood clotting (e.g., venous thromboembolus and the like) that can arise as a side effect of certain drugs. In therapeutic applications, the ST3Gal IV inhibitors of the invention are administered to an individual already suffering from atherosclerosis or a related condition. Compositions that contain the inhibitors are administered to a patient in an amount sufficient to decrease the amount of ST3Gal IV activity, and to cure or at least partially arrest the symptoms and/or complications of the atherosclerosis. For example, the ST3Gal IV inhibitors can arrest the further development of the atherosclerosis. An amount adequate to accomplish this is defined as "therapeutically effective dose." Amounts effective for this use will depend on, e.g., the inhibitor composition, the manner of administration, the stage and severity of the disease being treated, the weight and general state of health of the patient, and the judgment of the prescribing physician. Therapeutic administration can begin at the first sign of disease or the detection or shortly after diagnosis in the case of atherosclerosis. This is often followed by repeated administration until at least symptoms are substantially abated and for a period thereafter.

Certain drugs can cause blood clotting as a side effect. These drugs include, for example, anticancer treatments such as tamoxifen, as well as corticosteroids, raloxifene, and birth control agents (such as estrogens and progestins). To prevent blood clots that could otherwise result from administration of these and other drugs that have this side effect, the sialyltransferase inhibitors are preferably administered before or simultaneously with the administration of the clot-forming drug, although one can also administer the ST3Gal IV inhibitors after the drug is administered. Once a blood clot has formed as a result of such treatment, one can administer the inhibitors to reduce the clot or slow its further development.

Therapeutically effective amounts of the ST3Gal IV inhibitor compositions of the present invention generally range, for the initial immunization (that is for therapeutic or prophylactic administration), from about 1.0 mg to about 10 g of ST3Gal IV inhibitor for a 70 kg patient, usually from about 10 mg to about 5 g, and preferably between about 2 mg and about 1 g. These doses can be followed by repeated administrations over weeks to months depending upon the patient's response and condition by measuring immune system activity.

For prophylactic use, administration should be given to individuals that fall into groups that are at risk for developing atherosclerosis. A "prophylactic dose" is that which is effective to maintain the concentration of vWF at a desired level that is associated with reduced risk of atherosclerosis.

The pharmaceutical compositions for therapeutic or prophylactic treatment are intended for parenteral, topical, oral or local administration. Typically, the pharmaceutical compositions are administered parenterally, e.g., intravenously, subcutaneously, intradermally, or intramuscularly. Compositions of the invention are also suitable for oral administration. Thus, the invention provides compositions for parenteral administration which comprise a solution of the glycosyltransferase inhibiting agent dissolved or suspended in an acceptable carrier, preferably an aqueous carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of ST3Gal IV inhibiting agents of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The ST3Gal IV inhibitors of the invention can also be administered via liposomes, which serve to target the conjugates to a particular tissue, such as myeloid tissue, as well as increase the half-life of the peptide composition. Liposomes include emulsions, foams, micelles, insoluble monolayers, liquid crystals, phospholipid dispersions, lamellar layers and the like. In these preparations the inhibitor to be delivered is incorporated as part of a liposome, alone or in conjunction with a molecule which binds to, e.g., a receptor prevalent among myeloid cells, or with other therapeutic or immunogenic compositions. Thus, liposomes filled with a desired inhibitor of the invention can be directed to the site of myeloid cells, where the liposomes then deliver the selected ST3Gal IV inhibitor compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al. (1980) Ann. Rev. Biophys. Bioeng. 9: 467, U.S. Pat. Nos. 4,235,871, 4,501,728 and 4,837,028.

The targeting of liposomes using a variety of targeting agents is well known in the art (see, e.g., U.S. Pat. Nos. 4,957,773 and 4,603,044). For targeting to the immune cells, a ligand to be incorporated into the liposome can include, e.g., antibodies or fragments thereof specific for cell surface determinants of the desired target cells. A liposome suspension containing a peptide or conjugate can be administered intravenously, locally, topically, etc. in a dose which varies according to, inter alia, the manner of administration, the conjugate being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more conjugates of the invention, and more preferably at a concentration of 25%–75%.

For aerosol administration, the inhibitors are preferably supplied in a suitable form along with a surfactant and propellant. Typical percentages of ST3Gal IV inhibitors are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute 0.1%–20% by weight of the composition, preferably 0.25–5%. The balance of the composition is ordinarily propellant. A carrier can also be included, as desired, as with, e.g., lecithin for intranasal delivery.

Alternatively, DNA or RNA that inhibits expression of one or more glycosyltransferase inhibitors, such as an antisense nucleic acid or a nucleic acid that encodes a peptide that blocks expression or activity of ST3Gal IV can be introduced into patients to achieve inhibition. U.S. Pat. No. 5,580,859 describes the use of injection of naked nucleic acids into cells to obtain expression of the genes which the nucleic acids encode.

Preferably, the administration of the ST3 Gal IV inhibitors will result in a decrease in vWF, and a concomitant decrease in FVIII. During the course of treatment. levels of vWF are preferably monitored and the frequency and amounts of inhibitor administration are adjusted to maintain vWF at a desired level. For both therapeutic and prophylactic purposes, vWF levels in the blood are reduced by at least about 30% compared to normal levels in the absence of the sialyltransferase inhibitor, more preferably by at least about 40%, and still more preferably vWF levels are reduced to about 50% of the normal level. The levels of reduction in vWF levels obtainable using the methods of the invention is not sufficient to cause von Willebrand's disease, which is characterized by vWF levels that are less than about 10% of normal.

A reduction in ST3Gal IV activity of about 50% will typically achieve the desired level of vWF level. A much reduction of ST3Gal IV activity, for example, complete elimination of the ST3Gal IV, can cause a reduction in platelet formation. This can further decrease the development of undesired blood clots and is thus desirable for severe cases of atherosclerosis.

Diagnostic Methods

The present invention also provides methods of determining the degree of α2,3-sialylation by detecting the levels of α2,3 sialylgalactosides in a sample from a patient. The diagnostic methods are also useful for monitoring the effectiveness of a prophylactic or treatment regime for atherosclerosis-related conditions, for example. Samples that are suitable for use in the diagnostic methods of the invention include, for example, myeloid cells and other blood cells.

The methods involve contacting a sample from a patient or other animal with a detection moiety that binds to a particular oligosaccharide structure, e.g., an α2,3-sialylgalactoside. Standard methods for detection of desired carbohydrate structures are known. For instance, specific lectins or antibodies raised against oligosaccharide can be used. For example, members of the siglec family of lectins that bind to oligosaccharides that are terminated with α2,3-linked sialic acid are suitable. For example, the MAL II lectin, which can be isolated from *Maackia amurensis* seeds, is suitable.

Alternatively, rather than using a binding moiety that binds to the sialic acid-terminated oligosaccharides, one can employ a binding moiety that binds to the acceptor for the ST3Gal IV. In the absence of a particular sialyltransferase, the concentration of acceptor moieties tends to increase. Thus, decreased levels of ST3Gal IV activity will result in an increase in the concentration of such unsialylated acceptor moieties. For example, one can employ a lectin, antibody, or other moiety that binds to unsialylated Galβ1,4GlcNAc or Galβ1,3GalNAc. Lectins that are suitable for this purpose include, for example, peanut agglutinin (PNA) or *Erythrina cristagalli* (ECA) lectin.

Glycosyltransferases themselves, in particular the acceptor binding domain of a glycosyltransferase, are also useful as binding moieties in the diagnostic assays of the invention. A deficiency of ST3Gal IV sialyltransferase causes a dramatic increase in terminal galactose residues (i.e., Galβ1, 4GlcNAc-) on myeloid cells. Thus, one can use the ST3Gal IV sialyltransferase as a detection moiety to determine whether ST3Gal IV is deficient in the cells.

In typical embodiments, the detection moieties are labeled with a detectable label. The detectable labels can be primary labels (where the label comprises an element that is detected directly or that produces a directly detectable element) or secondary labels (where the detected label binds to a primary label, as is common in immunological labeling). An introduction to labels, labeling procedures and detection of labels is found in Polak and Van Noorden (1997) *Introduction to Immunocytochemistry,* 2nd ed., Springer Verlag, N.Y. and in Haugland (1996) *Handbook of Fluorescent Probes and Research Chemicals*, a combined handbook and catalogue published by Molecular Probes, Inc., Eugene, Oreg. Primary and secondary labels can include undetected elements as well as detected elements. Useful primary and secondary labels in the present invention can include spectral labels such as fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$P, etc.), enzymes (e.g., horse radish peroxidase, alkaline phosphatase etc.), spectral calorimetric labels such as colloidal gold or colored glass or plastic (e.g. polystyrene, polypropylene, latex, etc.) beads. The label can be coupled directly or indirectly to a component of the detection assay (e.g., the detection reagent) according to methods well known in the art. As indicated above, a wide variety of labels can be used, with the choice of label depending on sensitivity required, ease of conjugation with the compound, stability requirements, available instrumentation, and disposal provisions.

Preferred labels include those that use: 1) chemiluminescence (using horseradish peroxidase or luciferase) with substrates that produce photons as breakdown products as described above) with kits being available, e.g., from Molecular Probes, Amersham, Boehringer-Mannheim, and Life Technologies/Gibco BRL; 2) color production (using both horseradish peroxidase and/or alkaline phosphatase with substrates that produce a colored precipitate [kits available from Life Technologies/Gibco BRL, and Boehringer-Mannheim]); 3) hemifluorescence using, e.g., alkaline phosphatase and the substrate AttoPhos [Amersham] or other substrates that produce fluorescent products, 4) fluorescence (e.g., using Cy-5 [Amersham]), fluorescein, and other fluorescent tags]; 5) radioactivity. Other methods for labeling and detection will be readily apparent to one skilled in the art.

Preferred enzymes that can be conjugated to detection reagents of the invention include, e.g., luciferase, and horse radish peroxidase. The chemiluminescent substrate for luciferase is luciferin. Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl)spiro[1,2-dioxetane-3,2'-adamantane], which is detected with a luminometer. Embodiments of horse radish peroxidase substrates include 2,2'azino-bis(3-ethylbenzthiazoline-6 sulfonic acid) (ABTS), 5-aminosalicylic acid (5AS), o-dianisidine, and o-phenylenediamine (OPD), which are detected with a spectrophotometer; and 3,3,5,5'-tetramethylbenzidine (TMB), 3,3'diaminobenzidine (DAB), 3-amino-9-ethylcarbazole (AEC), and 4-chloro-1-naphthol (4C1N), which are detected visually. Other suitable substrates are known to those skilled in the art.

In general, a detector which monitors a particular label is used to detect the label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis.

Commercially available detection moieties that are suitable for use in the methods of the invention include SNA-fluorescein isothiocyanate (FITC) lectin (FL-1301, Vector Laboratories, Burlingame Calif.) and biotinylated SNA lectin (B-1305, Vector Laboratories) for α2,3 sialyl galactosides.

A reduction in ST3Gal IV activity is evidenced by a substantial reduction in α2,3-sialylgalactosides in a sample obtained from the patient. Alternatively, methods for detecting levels of ST3Gal IV enzymatic activities can be used. As used herein, a "substantial reduction" in the appropriate sialylgalactoside levels or ST3GAl IV activity refers to a reduction of at least about 30% in the test sample compared to a non-immunodeficient control. Depending on the degree of reduction in vWF levels desired, the reduction in ST3Gal IV activity or α2,3-linked sialylgalactoside will be at least about 50%, more preferably at least about 75%, and most preferably sialylgalactoside or ST3Gal IV levels will be reduced by at least about 90% in a sample from an animal that has a clotting disorder compared to a control. Again, however, monitoring of vWF/FVIII levels is the preferred method of monitoring the effectiveness of a treatment or prophylactic administration.

Transgenic Animals that Lack ST3Gal IV Sialyltransferase

The invention also provides eukaryotic cells, as well as chimeric and transgenic nonhuman animals which contain cells, that lack at least one ST3Gal IV gene that is typically found in wild-type cells of the animal. Methods for producing such cells and animals are also provided. These cells and animals are useful for several purposes, including the study of the mechanisms by which vWF and FVIII are involved in blood clotting, atherosclerosis and VWD. The "knockout" cells and animals can also be used for producing glycoproteins and glycolipids that, when produced in a wild-type cell or animal, would carry an α2,3-linked sialic acid residue that is not desirable for a particular application.

A "chimeric animal" includes some cells that lack the functional sialyltransferase gene of interest and other cells that do not have the inactivated gene. A "transgenic animal," in contrast, is made up of cells that have all incorporated the specific modification which renders the sialyltransferase gene inactive. While a transgenic animal is capable of transmitting the inactivated sialyltransferase gene to its progeny, the ability of a chimeric animal to transmit the mutation depends upon whether the inactivated gene is present in the animal's germ cells.

The modifications that inactivate the sialyltransferase gene can include, for example, insertions, deletions, or substitutions of one or more nucleotides. The modifications can interfere with transcription of the gene itself, with translation and/or stability of the resulting mRNA, or can cause the gene to encode an inactive sialyltransferase polypeptide. For example, a mutation can be introduced into the promoter region of one or more ST3Gal IV genes, in which case the gene is expressed at a reduced level, if at all. Alternatively, the coding region of the gene can be mutated.

The methods of the invention are useful for producing transgenic and chimeric animals of most vertebrate species. Such species include, but are not limited to, nonhuman mammals, including rodents such as mice and rats, rabbits, ovines such as sheep and goats, porcines such as pigs, and bovines such as cattle and buffalo. Methods of obtaining transgenic animals are described in, for example, Puhler, A., Ed., *Genetic Engineering of Animals*, VCH Publ., 1993; Murphy and Carter, Eds., *Transgenesis Techniques: Principles and Protocols* (*Methods in Molecular Biology*, Vol. 18), 1993; and Pinkert, C A, Ed., *Transgenic Animal Technology: A Laboratory Handbook*, Academic Press, 1994.

One method of obtaining a transgenic or chimeric animal having an inactivated ST3Gal TV gene in its genome is to contact fertilized oocytes with a vector that includes a ST3Gal IV-encoding polynucleotide that is modified to contain an inactivating modification. For some animals, such as mice, fertilization is performed in vivo and fertilized ova are surgically removed. In other animals, particularly bovines, it is preferably to remove ova from live or slaughterhouse animals and fertilize the ova in vitro. See DeBoer et al., WO 91/08216. In vitro fertilization permits the modifications to be introduced into substantially synchronous cells. Fertilized oocytes are then cultured in vitro until a pre-implantation embryo is obtained containing about 16–150 cells. The 16–32 cell stage of an embryo is described as a morula. Pre-implantation embryos containing more than 32 cells are termed blastocysts. These embryos show the development of a blastocoel cavity, typically at the 64 cell stage. If desired, the presence of a desired inactivated ST3Gal IV gene in the embryo cells can be detected by methods known to those of skill in the art. Methods for culturing fertilized oocytes to the pre-implantation stage are described by Gordon et al. (1984) *Methods Enzymol.* 101: 414; Hogan et al. (1986) *Manipulation of the Mouse Embryo: A Laboratory Manual*, C.S.H.L. N.Y. (mouse embryo); Hammer et al. (1985) *Nature* 315: 680 (rabbit and porcine embryos); Gandolfi et al. (1987) *J. Reprod. Fert.* 81: 23–28; Rexroad et al. (1988) *J. Anim. Sci.* 66: 947–953 (ovine embryos) and Eyestone et al. (1989) *J. Reprod. Fert.* 85:715–720; Camous et al. (1984) *J. Reprod. Fert.* 72: 779–785; and Heyman et al. (1987) *Theriogenology* 27: 5968 (bovine embryos). Sometimes pre-implantation embryos are stored frozen for a period pending implantation. Pre-implantation embryos are transferred to an appropriate female resulting in the birth of a transgenic or chimeric animal depending upon the stage of development when the transgene is integrated. Chimeric mammals can be bred to form true germline transgenic animals.

Alternatively, the disrupted ST3Gal IV gene can be introduced into embryonic stem cells (ES). These cells are obtained from preimplantation embryos cultured in vitro. See, e.g., Hooper, M L, *Embryonal Stem Cells: Introducing Planned Changes into the Animal Germline* (Modern Genetics, v. 1), Int'l. Pub. Distrib., Inc., 1993; Bradley et al. (1984) *Nature* 309, 255–258. Transformed ES cells are combined with blastocysts from a nonhuman animal. The ES cells colonize the embryo and in some embryos form the germ line of the resulting chimeric animal. See, Jaenisch (1988) *Science* 240: 1468–1474. Alternatively, ES cells or somatic cells that can reconstitute an organism ("somatic repopulating cells") can be used as a source of nuclei for transplantation into an enucleated fertilized oocyte giving rise to a transgenic mammal. See, e.g., Wilmut et al. (1997) *Nature* 385: 810–813.

The introduction of the modified ST3Gal IV gene into recipient cells can be accomplished by methods known to those of skill in the art. For example, the modified gene can be targeted to the wild type ST3Gal IV locus by homologous recombination. Alternatively, a recombinase system can be employed to delete all or a portion of a locus of interest. Examples of recombinase systems include, the cre/lox system of bacteriophage P1 (see, e.g., Gu et al. (1994) *Science* 265: 103–106; Terry et al. (1997) *Transgenic Res.* 6: 349–356) and the FLP/FRT site specific integration system (see, e.g., Dymecki (1996) *Proc. Nat'l. Acad. Sci. USA* 93: 6191–6196). In these systems, sites recognized by the particular recombinase are typically introduced into the genome at a position flanking the portion of the gene that is to be deleted. Introduction of the recombinase into the cells then catalyzes recombination which deletes from the genome the polynucleotide sequence that is flanked by the recombination sites. If desired, one can obtain animals in which only certain cell types lack the sialyltransferase gene of interest. See, e.g., Tsien et al. (1996) *Cell* 87: 1317–26; Brocard et al. (1996) *Proc. Nat'l. Acad. Sci. USA* 93: 10887–10890; Wang et al. (1996) *Proc. Nat'l. Acad. Sci. USA* 93: 3932–6; Meyers et al. (1998) *Nat. Genet.* 18: 136–41).

EXAMPLES

The following example is offered to illustrate, but not to limit the present invention. Knockout mice were constructed in which genes encoding the ST3Gal-IV sialyltransferase were disrupted. Studies of these mice demonstrated that ablation of this ST3Gal-IV sialyltransferase, which acts on both N- and O-glycans in vitro, results in an autosomal dominant reduction in von Willebrand factor (vWF) in mice. This is concomitant with an autosomal recessive thrombocytopenia and an increase in bleeding time. These findings indicate that loss of a terminal sialic acid can result in an autosomal dominant phenotype which may provide insight into mechanisms underlying VWD.

Materials and Methods

Gene Targeting of the ST3Gal-IV and Production of Mutant Mice

Isolation of mouse ST3Gal-IV genomic DNA and construction of a targeting vector bearing Cre loxP recombination signals was accomplished in a manner similar to that described by (Priatel et al. (1997) *Glycobiology* 7: 45–56). R1 ES cells (Nagy et al. (1993) *Proc. Nat'l. Acad. Sci. USA* 90: 8424–8) were electroporated with 10 µg of the linearized targeting construct shown in FIG. 1A, and the resulting clones were screened by Southern blotting using the genomic probe (FIG. 1A). Targeted ES cells were electroporated with 5 µg of Cre expression plasmid and subclones bearing the ST3Gal-IV$^{-/-}$ and ST3Gal-IV$^F$ alleles (FIG. 1B) were isolated. ST3Gal-IV$^{-/-}$ and ST3Gal-IV$^{-/-}$ chimeric mice were generated using standard techniques (Metzler et al. (1994) *EMBO J.* 13: 2056–65) and were crossed into the C57BL/6 background for the generation of heterozygous and homozygous offspring.

The ST3Gal-IV alleleic structure was analyzed by Southern blotting and PCR. The wild type ST3Gal-IV allele was detected using PCR primers adjacent to the deleted region (W5': 5'-GAC GCC ATC CAC CTA TGA G (SEQ ID NO:1) and W3': 5'-GGC TGC TCC CAT TCC ACT-3' (SEQ ID NO:2)) resulting in a 260 bp fragment, while the mutant allele was detected using W5' and a primer from the loxP region (M3': 5'-GGC TCT TTG TGG GAC CAT CAG-3' (SEQ ID NO:3)), yielding a 450 bp fragment.

Northern Blot Analysis

Total RNA from a panel of tissues obtained from a wild-type mouse, and from small intestine and colon of wild-type and ST3Gal-IV$^{-/-}$ mice was isolated by cesium chloride density centrifugation. Five µg of total RNA was electrophoresed on a denaturing 1% agarose gel and transferred to nitrocellulose. Detection of the ST3Gal-IV message was accomplished by hybridizing to the labeled full-length ST3Gal-IV cDNA.

Flow Cytometry

Single cell suspensions of splenocytes were prepared and erythrocytes removed by ammonium chloride lysis. Cells were incubated in the presence of antibodies (below) in FACS buffer (2% FCS in PBS) for 20 minutes at 4° C. For sialoadhesin and selectin binding, cells were treated with 0.5 µg/ml of Fc Block (anti-CD32/16, PharMingen), then incubated with Gr-1 and a sialoadhesin-IgC chimera or selectin-IgM chimeras (Ellies et al. (1998) *Immunity* 9: 881–90) with or without addition of 5 mm EDTA for 30 minutes at 4° C. Cells were washed and incubated with a goat anti-human FITC conjugated secondary antibody (Sigma) as appropriate. Antibodies used CD43 (S7 and 1B11), Gr-1 (RB6-8C5) (PharMingen). Data were analyzed on a FACScan™ flow cytometer using CELLQUEST™ software (Becton Dickinson).

Hematology

Blood from the tail vein of methoxyfluorane anesthetized mice was collected into EDTA-coated polypropylene microtubes (Becton Dickinson). Analyses of red blood cells, white blood cells and platelet cell numbers and morphology were carried out manually and with a CELL-DYN3500™ calibrated with normal mouse blood (UCSD Medical Center, Hillcrest).

For the preparation of plasma samples, whole blood was collected by cardiac puncture in one-tenth of volume buffered citrate anticoagulant (0.065 mol/l sodium citrate, 0.045 mol/l citric acid, pH 7.4). Platelet-poor plasma was prepared by centrifugation twice at 1800 g for 15 min at room temperature and stored at −80° C. Normal reference mouse plasma (NMP) was prepared by pooling plasma, prepared as above, from 10–20 individual C57B1/6 mice. All clotting times were performed on a Diagnostica Stago ST4™ semi-automated coagulometer (American Bioproducts, Parsippany, N.J.). Chromogenic substrate based assays were performed on a Molecular Device microtiter plate reader which recorded either the rate of change in optical density (mOD/min) or simple endpoint color density (mOD).

Prothrombin Time (PT)

Thirty microliters of plasma was incubated at 37° C. for 3 min. Then 60 µl of prewarmed thromboplastin reagent (Thromboplastin C-Plus™, Baxter, Miami, Fla.) was added to initiate clotting.

Activated Partial Thromboplastin Time (aPTT)

Thirty microliter of plasma was incubated with 30 µl of a PTT reagent (Automated APTT™, Organon Technika, N.C.) for 5 min at 37° C. Following this, 30 µl of prewarmed 25 mM calcium chloride was added to initiate clotting.

Thromboplastin-Based Assays

Prothrombin (Factor II) Activity Assay

Thirty µl of test plasma, diluted 1:20 in 25 mM Hepes (pH 7.5), 150 mM NaCl (HN buffer), were incubated for 3 min at 37° C. with 30 µl of a 1:1 mixture of prothrombin-depleted plasma reagent (Diagnostica Stago™, Asnieres, France) and rabbit barium adsorbed plasma (Hemostasis part VIII. Principles of Coagulation Tests). Clotting was then initiated by the addition of 60 µl of Thromboplastin C-Plus™. Clotting times were converted to percent reference mouse plasma prothrombin from a log—log standard curve prepared with dilutions between 1:5 and 1:80 in HN buffer of NMP. Standard curves were prepared on each day of testing.

Factor VII Activity Assay

The assay was carried out exactly as for the factor II assay except that a congenital human factor VII deficient plasma was used.

Factor V Activity Assay

The Factor V activity assay was carried out as for the factor II assay except that: (1) 30 µl of a human factor V immunodepleted plasma reagent (American Diagnostica Inc., Greenwhich, Conn.) was used without mixing 1:1 with barium adsorbed rabbit plasma; (2) the samples were diluted 1:200 in HN buffer; and (3) the standard curves were made with dilutions between 1:50 to 1:1000.

Activated Partial Thromboplastin Time-Based Assays

Factor VIII Activity Assay

Thirty µl of test plasma, diluted 1:20 in HN buffer, were incubated for 5 min at 37° C. with 30 µl of human congenital factor VIII deficient plasma and 30 µl of aPTT reagent. Clotting was then initiated with the addition of 30 µl of 25 mM calcium chloride. The clotting times were converted to percent reference mouse plasma factor VIII from a log—log standard curves made from NMP diluted 1:5 to 1:80 in HN buffer.

Factors IX, XI, and XII Activity Assays

These assays were performed exactly as described for the factor VIII assays except that the corresponding human factor deficiency plasma were used.

Von Willebrand Antigen Assay

A 96-well microtiter plate was coated overnight at 4° C. with 200% of 10 µg/ml rabbit anti-human vWF polyclonal antibody (Dako Inc, Denmark) prepared in 50 mM $Na_2CO_3$, pH 9.6. The wells were then blocked with 25 mM Tris, pH 7.5, 150 mM NaCl containing 3% BSA (TBS/3% BSA) for 2 h at 37° C. After washing with TBS/1% BSA, 100 µl aliquots of test plasmas diluted 1:100 and 1:200 in TBS/1% BSA were incubated in the wells for 2 h at 37° C. After washing 5 times with TBS containing 0.05% Tween 20, the wells were incubated with 100 µl of horse radish peroxidase-conjugated rabbit anti-human vWF polyclonal antibodies (Dako Inc) diluted 1:2000 in TBS/1% BSA for 1 h at 37° C. After washing 5 times with TBS/0.05% Tween 20, color was developed using a BioRad Peroxidase substrate kit according to the manufacturer's instruction and read at 405 nm. A standard curve was constructed with each plate by diluting NMP 1:10 to 1:250 in TBS/1% BSA.

Protein C and Protein S Antigen Assays

These assays were performed as described for the vWF antigen assay using polyclonal rabbit anti-human protein C or protein S (Dako Inc, Denmark) respectively, in place of the vWF antibody.

Antithrombin Activity Assay

Forty µl of test plasma samples diluted 1:40 and 1:80 in Hepes, pH 7.5, 150 mM NaCl and 0.1% BSA (HN/BSA) were incubated in microtiter plate wells with 40 µl factor Xa/heparin reagent (3 µg/ml factor Xa (Enzyme Research Lab, IN) and 10 U/ml unfractionated heparin) for 3 min at 37° C. Then 40 µl of 1.25 ml/ml chromogenic substrate S-2765 (DiaPharma, Ohio) was added to each well and the color developed was read at 405 nm. Standard curves were prepared with each plate by diluting NMP 1:20 to 1:640 in HN/BSA.

Tail Bleeding Time

Mice were anesthetized and laid horizontally within a brass block to restrict body movement. The tail was severed ~2 mm from the tip with a razor blade and immersed vertically ~1 cm below the surface of saline warmed to 37° C. The time taken for the bleeding to stop was recorded as the tail bleeding time. The tail was cauterized for bleeding times in excess of 10 minutes.

Immunohistochemistry

Frozen sections of spleen or small intestine were fixed, permeabilized and blocked as previously described (Nichols, W. Cell 1998). The DBA-FITC lectin at 5 µg/ml and vWF antibody at 25 µg/ml were applied to the sections in PBS with 0.05% Tween 20™, 0.05% Triton X-100™ and 5% goat serum and incubated overnight at 4° C. The slides were washed three times in PBS and a goat anti-rabbit rhodamine secondary antibody (Jackson) was applied for 1 h. After three washes in PBS the slides were air dried and mounted with Gel/Mount™ (Biomeda, Foster City, Calif.). Bone marrow hematoxylin and eosin slides were prepared from cytospins of single cells suspensions.

Platelet Clearance

Platelets from wild type or mutant mice were biotinylated in vivo as previously described (Ault and Knowles (1995) *Exp. Hematol.* 23: 996–1001; Manning et al. (1996) *Lab. Anim Sci.* 46: 545–8) using biotin-NHS (Calbiochem, La Jolla, Calif.). Blood from the tail vein was stained with anti-CD41 and streptavidin PE and analyzed by flow cytometry daily for 5 days to determine the percentage of labeled platelets remaining in the circulation. In other studies, splenectomies were performed on control or null ST3Gal-IV mice and hematologic profiles analyzed at various timepoints following surgery.

Multimer Analysis

Plasma samples were diluted 1:20 in 10 mM Tris-HCl and 1 mM EDTA pH 8.0 and assayed as previously described (Denis et al. (1998) *Proc. Nat'l. Acad. Sci. USA* 95: 9524–9). Multimers were detected by incubating the dried Gelbond™ with a $^{125}$I-labeled anti-human vWF antibody and visualized by autoradiography.

Lectin Blotting

ECA bound to agarose was used to immunoprecipitate vWF from whole cell lysates of control and ST3Gal-IV null lung and small intestine. Following electrophoresis on a 5% Tris-HCl polyacrylamide gel the protein was transferred to nitrocellulose and probed with an anti-human vWF antibody.

vWF Clearance

To observe vWF clearance, release from endothelial cells was stimulated by intravenous injection of 5 ng LPS. Tail bleeds were performed over a period of 4 h and vWF detected by ELISA.

Statistical Analysis

Data were analyzed by ANOVA and Scheffe's t test for unpaired samples using StatView® software.

Results

Disruption of ST3Gal-IV Gene by Targeted Mutagenesis

The ST3Gal-IV sialyltransferase is a type II Golgi enzyme that belongs to a family of six conserved members. A mouse genomic clone encompassing the twelve exon protein-coding region of the gene was used in constructing a gene-targeting vector designed to control exon deletion by Cre-loxP recombination (FIG. 1A). Homologous recombination of the targeting vector in embryonic stem (ES) cells incorporated selection markers and 3 loxP sites for the subsequent production of systemic ST3Gal-IV$^{-/-}$ or conditional ST3Gal-IV$^F$ mutations in vivo (FIGS. 1B and 1C). These alleles were transmitted into the mouse germline and offspring homozygous for either the ST3Gal-IV$^{-/-}$ or ST3Gal-IV$^F$ allele were generated. Such offspring, which occurred at a frequency of 25% of littermates, lacked overt physical or behavioral abnormalities, developed normally and were fully fertile. Mice homozygous for ST3Gal-IV$^{-/-}$ allele were further analyzed.

ST3Gal-IV mRNA Levels and Terminal Sialic Acid Production

Figure 2:
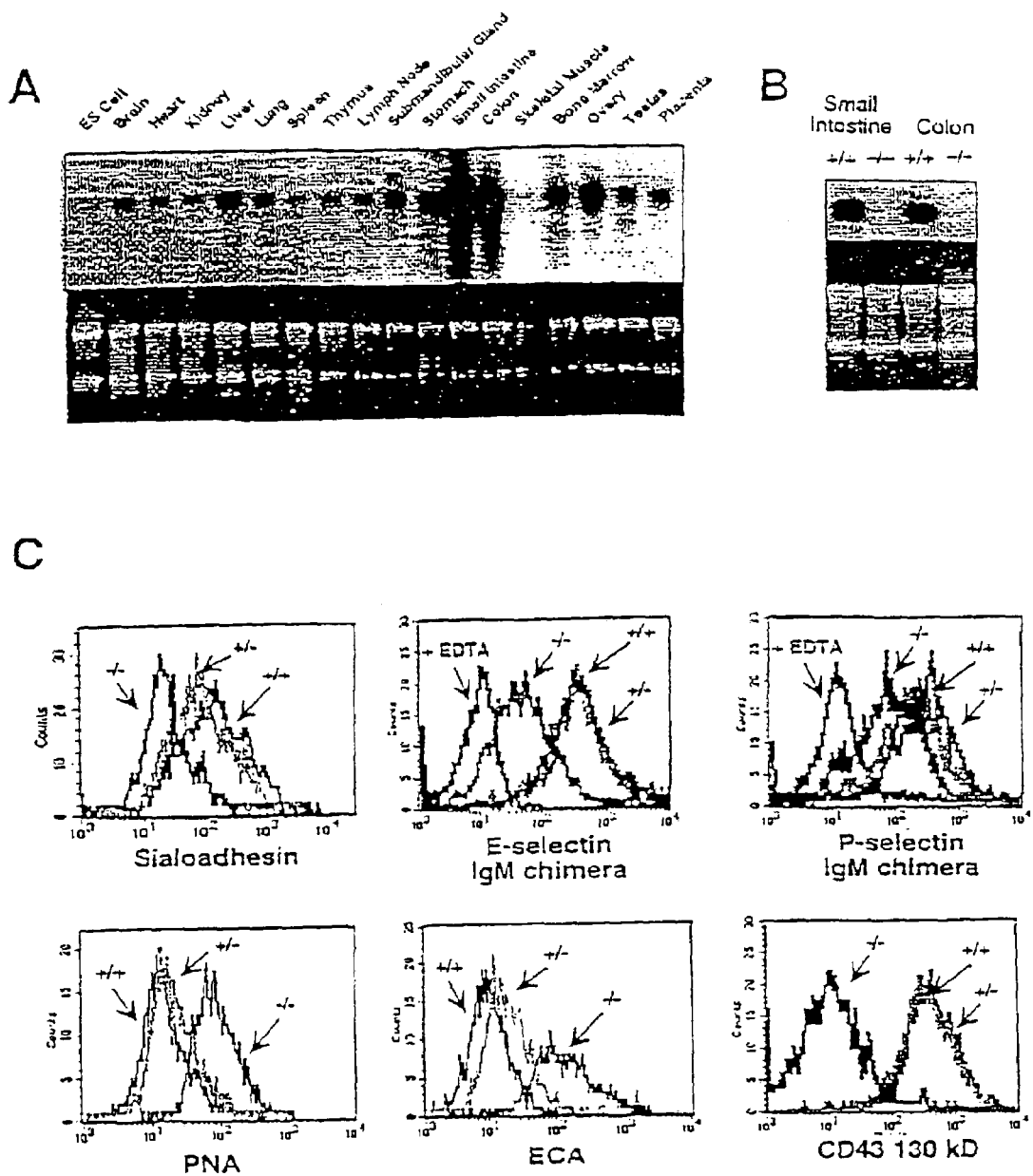
FIGS. 2A–C show ST3Gal-IV expression in various tissues of the knockout mice, as well as an analysis of the oligosaccharide structures present on myeloid cells obtained from homozygous normal (+/+), heterozygous (+/−), and homozygous ST3Gal-IV deficient (−/−) mice.

ST3Gal-IV mRNA as detected by Northern blotting is broadly expressed in mouse tissues and is highly expressed in the gastrointestinal tract (FIG. 2A). ST3Gal-IV$^{-/-}$ mice show a loss of mRNA from the small intestine and colon, suggesting that in these tissues the mRNA formed is unstable (FIG. 2B).

Several members of the siglec (sialoadhesin) family of lectins bind α2,3 sialic acids, although specific counter-receptors have not been defined (Crocker et al. (1997) *Glycoconj. J.* 14: 601–9). Myeloid cells of homozygous null (−/−) mice exhibited abrogation of siglec 1 binding (FIG. 2C)). This suggested that the ST3Gal-IV sialyltransferase is a key component of the binding site for this lectin, which has been proposed to be involved in myeloid cell function. Also observed was a significant loss of E-selectin binding and a minor reduction in P-selectin binding (FIG. 2C), which indicate that ST3Gal-IV is involved in selectin ligand formation, although other α2,3 sialyltransferases may be compensating for the majority of this activity.

Lymph node development and cellularity was normal as determined by histologic analysis, FACS and cell counting, and therefore L-selectin binding was not assessed in these mice.

An increase was observed in binding of peanut agglutinin (PNA) and *Erythrina cristagalli* (ECA) lectin binding, which recognize Galβ1,3GalNAc and Galβ1,4GlcNAc respectively, to myeloid cells from the bone marrow and spleen. This indicates an increase in exposure of terminal galactose, thus confirming the loss of a subset of terminal α2,3 sialic acids from cell surface glycoproteins on cells of the myeloid lineage (FIG. 2C). Interestingly, an epitope normally found on core 2 O-glycans of the cell surface adhesion molecule CD43, which is recognized by the 1B11 mAb, was absent in ST3Gal-IV$^{-/-}$ mice.

ST3Gal-IV Deficiency Results in a Moderate Thrombocytopenia and Mild Anemia

Hematologic examination revealed mild to moderate alterations in erythroid, lymphoid and myeloid lineages in ST3Gal-IV deficient mice. Total red blood cell counts and hemoglobin and hematocrit values were reduced approximately 8% compared with controls indicating a mild anemia in the ST3Gal-IV null mice. While no difference in WBC parameters were detected using the automated cell counter, more detailed flow cytometric analysis of lymphoid cells showed a 50% reduction in CD8 T lymphocytes in the thymus and a 25% reduction in the periphery. No deficits in T cell proliferation or cytotoxicity were detected.

Figure 3:
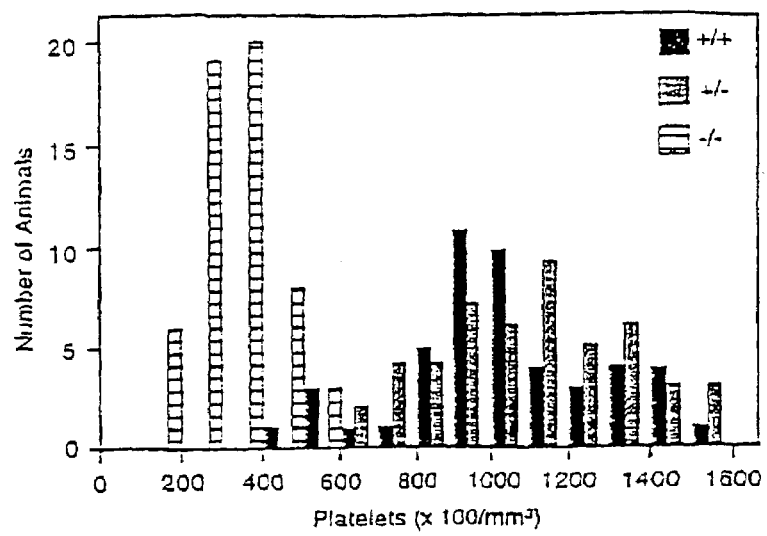
FIGS. 3A–C show the peripheral hematology in ST3Gal-IV deficient mice. The data shown in FIGS. 3A and 3B were obtained using blood collected from the tail vein of 6–8 week old mice. Automated platelet counts were carried out using a CELL-DYN 3500 and Wright-Giemsa stained smears. Counts from 20 mice of each genotype are expressed as cells per ml of whole blood±SEM (FIG. 3A).
Figure 3:
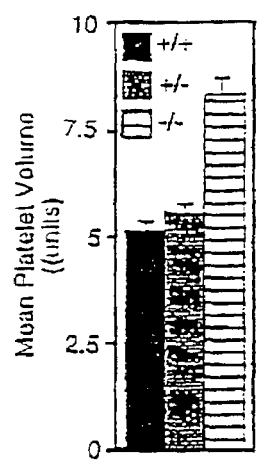
Figure 3:
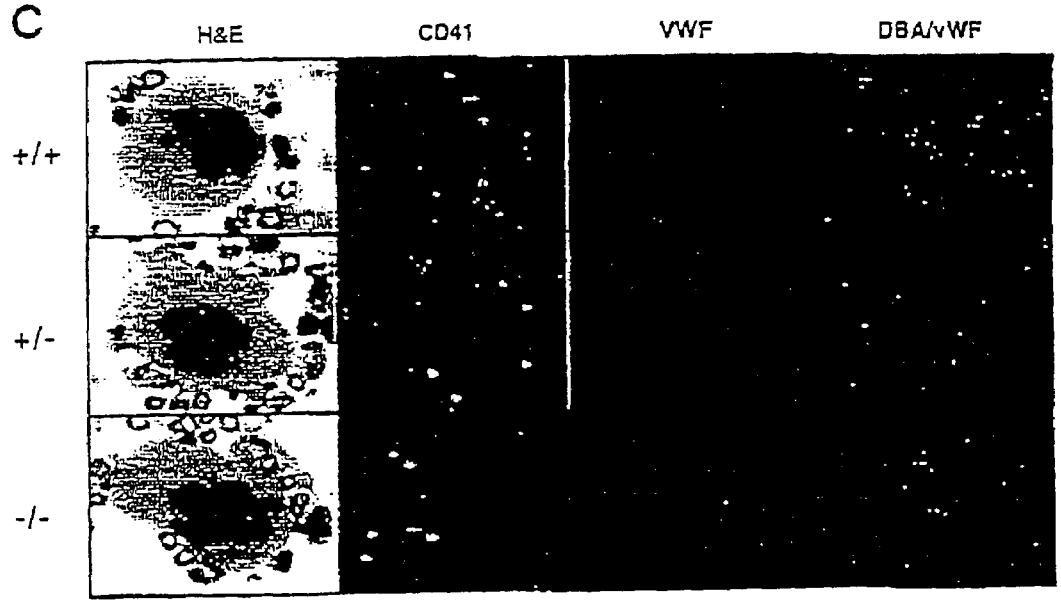

A moderate thrombocytopenia was noted in homozygous null mice, with platelet numbers being approximately one third of normal (FIG. 3A). Platelets were enlarged in size (FIG. 3B) suggesting a more immature status, however, hematoxylin and eosin as well as acetylcholinesterase staining indicated that mature megakaryocytes were present in the spleen and bone marrow (FIG. 3C). Analyses of serum biochemistry indicated normal renal function.

ST3Gal-IV Participates in Hemostasis

Figure 4:
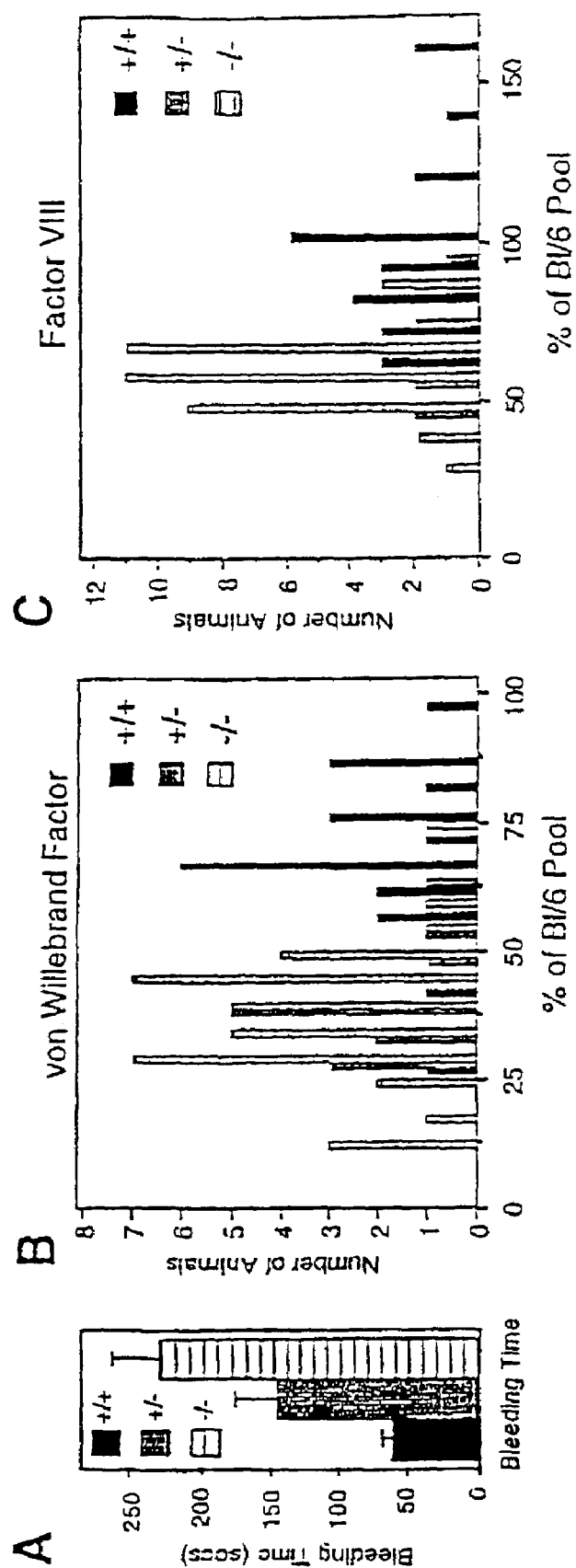
FIG. 4A shows the bleeding time of homozygous normal (+/+), heterozygous (+/−), and homozygous ST3Gal-IV deficient (−/−) mice.
FIGS. 4B and 4C show circulating levels of vWF and FVIII, respectively. Both vWF and FVIII were analyzed by ELISA from plasma samples.

To examine whether the ST3Gal-IV plays a role in hemostasis, the bleeding time of control, heterozygous and null mice was assessed. A significant increase in bleeding time was observed in ST3Gal-IV$^{-/-}$ mice (FIG. 4A). To distinguish whether the intrinsic or extrinsic clotting pathways were involved, the prothrombin time (PT) and activated partial thromboplastin time (aPTT) were determined. A significant increase in aPTT implicated a factor(s) in the intrinsic pathway. Accordingly, ATII, FGN, FII, FV, FVII, FVIII, FIX, FXI,

TABLE 1

|  | ST3Gal-IV$^{+/+}$ | ± SEM | ST3Gal-IV$^{-/-}$ | ± SEM |
| --- | --- | --- | --- | --- |
| PT | 10.16 | 0.08 | 10.44 | 0.07 |
| APTT | 24.46 | 0.41 | 25.58 | 0.33* |
| ATIII | 117.71 | 8.23 | 95.58 | 5.47 |
| FGN | 263.63 | 5.89 | 254.91 | 18.18 |
| FII | 101.75 | 4.52 | 99.56 | 3.6 |
| FV | 120.33 | 5.92 | 115.28 | 3.85 |
| FVII | 98 | 7.09 | 81.42 | 5.29 |
| FIX | 99.54 | 5.33 | 98.62 | 5.76 |
| FXI | 59.7 | 4.47 | 57.69 | 3.6 |
| FXII | 84.5 | 6.06 | 91.22 | 2.03 |
| Prot C | 115.65 | 27.04 | 109.73 | 21.6 |
| Prot S | 95.45 | 3.53 | 94.57 | 6.26 |
| PGN | 129.46 | 4.67 | 116.14 | 4.49 |
| a-2AP | 131.25 | 3.61 | 124.27 | 3.45 |

FXII, vWF, Prot. S, PGN and a-2AP were measured (Table 1). Surprisingly, we observed an autosomal dominant effect of the loss of ST3Gal-IV on vWF and its associated molecule, FVIII (FIGS. 4B and 4C, respectively). No differences in the levels of the other factors tested were noted.

ST3Gal-IV Deficient Platelets Have a Normal Life Span

Figure 5:
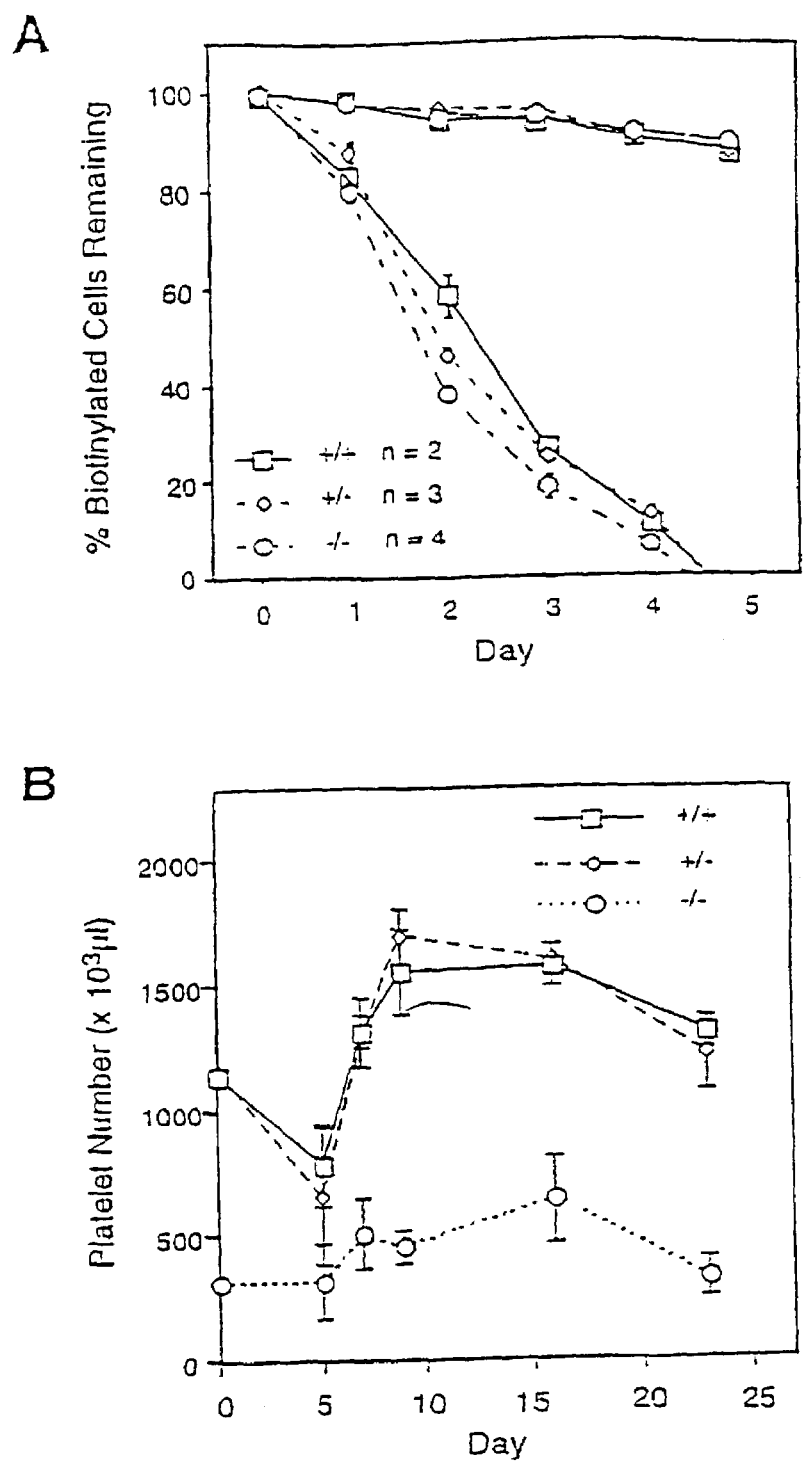
FIG. 5A shows the life span of biotinylated platelets, which was analyzed by flow cytometry.
FIG. 5B shows platelet numbers, as analyzed following splenectomy in wild type (+/+), heterozgous (+/−) or null (−/−) mice.
Figure 6:
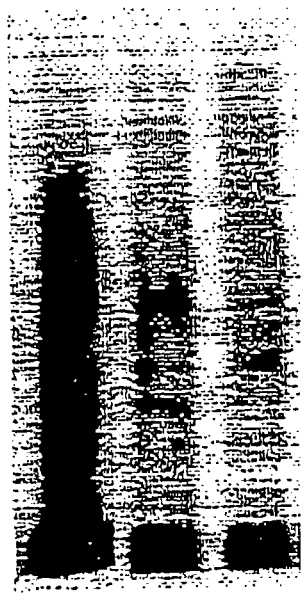
FIG. 6A shows an analysis of the clearance of vWF multimers.
FIG. 6B shows the clearance of vWF following LPS-elicited secretion.
Figure 6:
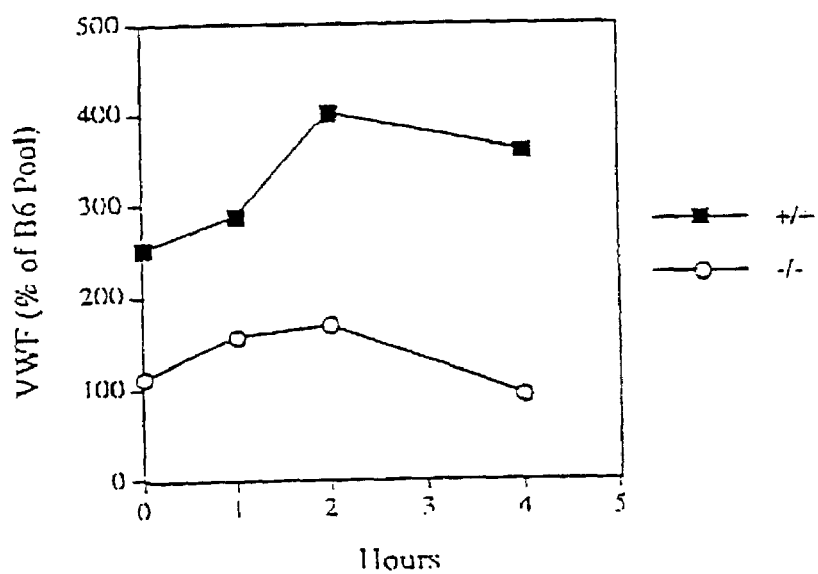

To study the clearance rate of platelets from the blood, platelets were labeled by in vivo biotinylation and followed by daily FACS analysis over the time course of their disappearance from the circulation. No difference was observed in the rate of turnover between wild type and ST3Gal-IV mutant mice (FIG. 5A). Although no splenomegaly was observed in ST3Gal-IV$^{-/-}$ mice, splenectomies were performed on control and ST3Gal-IV null mice to determine whether sequestration of platelets in the spleen could account for the reduced level of platelets. Preoperative spleen sizes were normal and no long term effect of splenectomy on platelet numbers was observed suggesting that this was not the mechanism involved in reduced platelet counts (FIG. 5B).

Aberrantly Glycosylated Endothelial Cell vWF is Rapidly Cleared from the Circulation Analysis of vWF protein in plasma samples confirmed that levels of vWF were reduced in heterozygous and homozygous null mice and indicated that normal multimeric structures were present. To detect abnormal forms of vWF, ECA lectin immunoprecipitations of endothelial cell vWF from lung and small intestine are carried out and probed with an anti-vWF antibody. The rate of clearance from the circulation of this abnormal vWF is assessed by stimulating vWF secretion with LPS and then following the loss of vWF from the circulation over time.

DISCUSSION

The finding that ablation of an α2,3 sialyltransferase can result in an autosomal dominant reduction of vWF to levels comparable to those observed in human VWD is of interest since the molecular mechanisms involved in the variable expression of this disease are not well understood. The decrease in vWF in ST3Gal-IV heterozygous and null mice is suggestive of a gain-of-function mutation, as evidenced by the similarity to the RIIIs/J mouse strain which has low plasma vWF. In the RIIIs/J mouse strain, the N-acetylgalactosaminyl-transferase Galgt2 is expressed in endothelial cells, rather than epithelial cells as it is in normal mouse strains. Because vWF is stored in endothelial cells, this results in enhanced clearance of vWF from this strain. This gain-of-function mutation results in Galgt2 expression in both heterozygous and homozygous null mice and thus has an autosomal dominant inheritance pattern.

A gain-of-function mutation is usually the result of changes in the protein coding sequence leading to new or altered functions (Wilkie (1994) *J. Med. Genet.* 31: 89–98). This seems unlikely for the ST3Gal-IV however, as Northern analysis shows that the highly vascular small intestine and colon, which express the highest levels of ST3Gal-IV message, have a complete loss of ST3Gal-IV RNA in ST3Gal-IV$^{-/-}$ strains (FIG. 2B). In addition, vWF mRNA levels as detected by RT-PCR are normal in all genotypes.

A more likely explanation for the autosomal dominant effect on this particular aspect of the phenotype is that loss of the ST3Gal-IV in endothelial cells results in a dominant negative mutation. Multimeric proteins such as vWF, which are dependent on oligomerization for activity, are the most susceptible to this mechanism (Herskowitz, I. (1987) *Nature* 329: 219–222). We hypothesize that in both the heterozygous and homozygous null mice, a reduction in or loss of ST3 Gal-IV activity results in mutant subunits that fail to oligomerize correctly. Treatment of human endothelial cells with tunicamycin to inhibit N-linked glycosylation results in a phenotype of severe VWD and an absence of secreted vWF (Wagner et al. (1986) *J. Cell Biol.* 102: 1320–4). A less severe phenotype would be expected in the ST3Gal-IV null mice, as this enzyme could potentially terminate only 40–60% of the Galβ1,4GlcNAc available on N-glycans (Sodetz et al. (1978) *J. Biol. Chem.* 253: 7202–6). Interestingly, acidic pH has been shown to be important for the successful polymerization of vWF (Wagner et al. (1986), supra.). Since sialic acid carries a net negative charge, part of its function may be to provide the correct acidic microenvironment for multimerization to occur.

An uncommon variant of VWD is Type 2B, in which patients have thrombocytopenia in addition to decreased vWF (Ruggeri et al. (1980) *J. Clin. Invest.* 65: 1318–25). The autosomal recessive reduction in circulating platelets as well as normal plasma vWF multimer formation suggest that the ST3Gal-IV deficient mice are not a model for this subtype. The platelet reduction did not correlate with the increase in bleeding time observed in these mice, although it did appear to contribute to the enhanced bleeding time in ST3Gal-IV$^{-/-}$ mice.

Thrombopoietin is the primary physiologic regulator of platelet formation, and a similar reduction in platelets is observed in mice lacking either thrombopoietin or its receptor (Carver-Moore et al. (1996) *Blood* 88: 803–8; Gurney et al. (1994) *Science* 265: 1445–7). These mice also exhibit a profound reduction in the number and size of megakaryocytes in the spleen and bone marrow, a phenotype not observed in the ST3Gal-IV null mice. Megakaryocyte numbers appear normal in ST3Gal-IV$^{-/-}$ mice and platelet clearance is not enhanced in vivo, suggesting that platelet formation is affected. The severe thrombocytopenia observed in mice lacking the transcription factor NF-E2 is due to the inability of megakaryocytes in these animals to produce proplatelets (Lecine et al. (1998) *Blood* 92: 1608–16). A similar mechanism may be occurring in the ST3Gal-IV mutant mice.

The ST3Gal-IV mice show a loss of the siglec 1 ligand on myeloid cells. Although no specific function has been assigned to this α2,3 sialic acid binding protein, it has been implicated in myeloid cell development (Crocker et al. (1997) *Glycoconj. J.* 14: 601–9). A role for the ST3Gal-IV in selectin ligand formation was confirmed in these studies and it will be interesting to determine whether the E-selectin ligand resides on N- or O-glycans as the identity of E-selectin ligands is controversial. The majority of E- and P-selectin ligands in mice reside on O-glycans as determined by deletion of the C2 GlcNAcT enzyme responsible for the branching of O-glycans (Ellies et al. (1998) *Immunity* 9: 881–90). It is possible that overlapping activities with the ST3Gal-III and ST3Gal-VI enzymes result in a moderate loss of E-selectin ligands and minimal loss of P-selectin ligands in these mice. Alternatively, only a subpopulation of E- and P-selectin ligands may be sialylated.

The apparent requirement for ST3Gal-IV activity in the normal formation of circulating vWF multimers indicates that this enzyme is a good target for drug therapy since a reduction in activity can affect vWF without affecting platelet formation. FVIII has been found to be a risk factor for coronary artery disease and blood group O individuals who have low serum cholesterol. Individuals with low vWF/FVIII have a low frequency of peripheral arterial disease compared with the general population (Hall et al. (1971) *Atherosclerosis* 14: 241–6; Meade et al. (1980) *Lancet* 1: 1050–4). Partial inhibition of the ST3Gal-IV can provide a similar benefit in disorders involving increased thrombosis. Interestingly, in vitro studies have implicated the ST3Gal-IV and ST3Gal-VI in the formation of selectin ligands which are involved in mediating cell—cell adhesion through binding to E-, P, or L-selectin (Okajima et al., (1999) *J. Biol. Chem.* 274: 11479–86; Sasaki et al. (1993) *J. Biol. Chem.* 268: 22782–7).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method for decreasing levels of vWF or FVIII in an animal, the method comprising
administering to the animal an effective dose of an inhibitor of ST3Gal-IV sialyltransferase enzyme activity, wherein said inhibitor is an analog of a ST3Gal-IV substrate and said animal is suffering from atherosclerosis or a blood clotting disorder, and whereby levels of von Williebrand factor (vWF) or factor VIII (FVIII) in the animal are decreased.

2. The method of claim 1, wherein the method is performed in conjunction with administration of a drug for which blood clotting is a potential side effect.

3. The method of claim 2, wherein the ST3Gal-IV sialyltransferase inhibitor is administered before or simultaneously with the drug for which blood clotting is a potential side effect.

4. The method of claim 1, wherein the method is performed as a therapeutic measure against atherosclerosis.

5. The method of claim 4, wherein the atherosclerosis is associated with coronary artery disease or peripheral arterial disease.

6. The method of claim 1, wherein platelet formation is not significantly affected by administration of the ST3Gal-IV sialyltransferase inhibitor to the animal.

7. The method of claim 1, further comprising monitoring the animal for levels of vWF or FVIII.

8. The method of claim 7, further comprising adjusting the dose of the ST3Gal-IV sialyltransferase inhibitor to maintain vWF at a desired level.

9. The method of claim 2, wherein the drug for which blood clotting is a potential side effect is selected from the group consisting of an anti-cancer drug, a corticosteroid, raloxifene, and a birth control agent.

10. The method of claim 9, wherein the anti-cancer drug is tamoxifen.

11. The method of claim 9, wherein the birth control agent is an estrogen or a progestin.

12. A method for modulating levels of vWF or FVIII in an animal, the method comprising
administering to the animal an effective dose of an inhibitor of ST3Gal-IV sialyltransferase enzyme activity, wherein said inhibitor is an analog of a ST3Gal-IV substrate and whereby levels of vWF or FVIII in the animal are decreased; and
monitoring the animal for levels of vWF or FVIII.

* * * * *

UNITED STATES PATENT AND TRADEMARK OFFICE
CERTIFICATE OF CORRECTION

| | | |
|---|---|---|
| PATENT NO. | : 7,192,914 B1 | |
| APPLICATION NO. | : 10/089525 | |
| DATED | : March 20, 2007 | |
| INVENTOR(S) | : Jamey D. Marth et al. | |

It is certified that error appears in the above-identified patent and that said Letters Patent is hereby corrected as shown below:

In the claims, column 27, line 34, kindly change

"1. A method for decreasing levels of vWF or FVIII in an animal, the method comprising administering to the animal an effective dose of an inhibitor of ST3Gal-IV sialyltransferase enzyme activity, wherein said inhibitor is an analog of a ST3Gal-IV substrate and said animal is suffering from atherosclerosis or a blood clotting disorder, and whereby levels of von Williebrand factor (vWF) or factor VIII (FVIII) in the animal are decreased.

2. The method of claim 1, wherein the method is performed in conjunction with administration of a drug for which blood clotting is a potential side effect.

3. The method of claim 2, wherein the ST3Gal-IV sialyltransferase inhibitor is administered before or simultaneously with the drug for which blood clotting is a potential side effect.

4. The method of claim 1, wherein the method is performed as a therapeutic measure against atherosclerosis.

5. The method of claim 4, wherein the atherosclerosis is associated with coronary artery disease or peripheral arterial disease.

6. The method of claim 1, wherein platelet formation is not significantly affected by administration of the ST3Gal-IV sialyltransferase inhibitor to the animal.

7. The method of claim 1, further comprising monitoring the animal for levels of vWF or FVIII.

UNITED STATES PATENT AND TRADEMARK OFFICE
CERTIFICATE OF CORRECTION

PATENT NO. : 7,192,914 B1
APPLICATION NO. : 10/089525
DATED : March 20, 2007
INVENTOR(S) : Jamey D. Marth et al.

It is certified that error appears in the above-identified patent and that said Letters Patent is hereby corrected as shown below:

In the claims, column 27, line 34, kindly change (cont'd)

8. The method of claim 7, further comprising adjusting the dose of the ST3Gal-IV sialyltransferase inhibitor to maintain vWF at a desired level.

9. The method of claim 2, wherein the drug for which blood clotting is a potential side effect is selected from the group consisting of an anti-cancer drug, a corticosteroid, raloxifene, and a birth control agent.

10. The method of claim 9, wherein the anti-cancer drug is tamoxifen.

11. The method of claim 9, wherein the birth control agent is an estrogen or a progestin.

12. A method for modulating levels of vWF or FVIII in an animal, the method comprising administering to the animal an effective dose of an inhibitor of ST3Gal-IV sialyltransferase enzyme activity, wherein said inhibitor is an analog of a ST3Gal-IV substrate and whereby levels of vWF or FVIII in the animal are decreased; and monitoring the animal for levels of vWF or FVIII."

to

--1. A method for decreasing levels of vWF or FVIII in an animal, the method comprising administering to the animal an effective dose of an inhibitor of ST3Gal-IV sialyltransferase enzyme activity, wherein said inhibitor is an analog of a ST3Gal-IV substrate and said animal is suffering from atherosclerosis or a blood clotting disorder, and whereby levels of von Williebrand factor (vWF) or factor VIII (FVIII) in the animal are decreased.

UNITED STATES PATENT AND TRADEMARK OFFICE
CERTIFICATE OF CORRECTION

| | | |
|---|---|---|
| PATENT NO. | : 7,192,914 B1 | |
| APPLICATION NO. | : 10/089525 | |
| DATED | : March 20, 2007 | |
| INVENTOR(S) | : Jamey D. Marth et al. | |

It is certified that error appears in the above-identified patent and that said Letters Patent is hereby corrected as shown below:

2. The method of claim 1, wherein the method is performed in conjunction with administration of a drug for which blood clotting is a potential side effect.
In the claims, column 27, line 34 kindly change (cont'd)

3. The method of claim 2, wherein the ST3Ga1-IV sialyltransferase inhibitor is administered before or simultaneously with the drug for which blood clotting is a potential side effect.

4. The method of claim 1, wherein the method is performed as a therapeutic measure against atherosclerosis.

5. The method of claim 4, wherein the atherosclerosis is associated with coronary artery disease or peripheral arterial disease.

6. The method of claim 1, further comprising monitoring the animal for levels of vWF or FVIII.

7. The method of claim 6, further comprising adjusting the dose of the ST3Gal-IV sialyltransferase inhibitor to maintain vWF at a desired level.

8. The method of claim 2, wherein the drug for which blood clotting is a potential side effect is selected from the group consisting of an anti-cancer drug, a corticosteroid, raloxifene, and a birth control agent.

9. The method of claim 8, wherein the anti-cancer drug is tamoxifen.

10. The method of claim 8, wherein the birth control agent is an estrogen or a progestin.

UNITED STATES PATENT AND TRADEMARK OFFICE
CERTIFICATE OF CORRECTION

PATENT NO. : 7,192,914 B1
APPLICATION NO. : 10/089525
DATED : March 20, 2007
INVENTOR(S) : Jamey D. Marth et al.

It is certified that error appears in the above-identified patent and that said Letters Patent is hereby corrected as shown below:

In the claims, column 27, line 34 kindly change (cont'd)

11. A method for modulating levels of vWF or FVIII in an animal, the method comprising administering to the animal an effective dose of an inhibitor of ST3Gal-IV sialyltransferase enzyme activity, wherein said inhibitor is an analog of a ST3Gal-IV substrate and whereby levels of vWF or FVIII in the animal are decreased; and monitoring the animal for levels of vWF or FVIII.--

Signed and Sealed this

Third Day of July, 2007

JON W. DUDAS
*Director of the United States Patent and Trademark Office*